(12) United States Patent
Shringarpure et al.

(10) Patent No.: US 10,747,899 B2
(45) Date of Patent: Aug. 18, 2020

(54) TECHNIQUES FOR DETERMINING WHETHER AN INDIVIDUAL IS INCLUDED IN ENSEMBLE GENOMIC DATA

(71) Applicant: The Board of Trustees of the Leland Stanford Junior University, Palo Alto, CA (US)

(72) Inventors: Suyash Shringarpure, Mountain View, CA (US); Carlos D. Bustamante, Emerald Hills, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 140 days.

(21) Appl. No.: 15/766,611

(22) PCT Filed: Oct. 6, 2016

(86) PCT No.: PCT/US2016/055717
§ 371 (c)(1),
(2) Date: Apr. 6, 2018

(87) PCT Pub. No.: WO2017/062599
PCT Pub. Date: Apr. 13, 2017

(65) Prior Publication Data
US 2018/0285593 A1    Oct. 4, 2018

Related U.S. Application Data

(60) Provisional application No. 62/242,081, filed on Oct. 15, 2015, provisional application No. 62/238,386, filed on Oct. 7, 2015.

(51) Int. Cl.
*G06F 21/62* (2013.01)
*G06F 16/00* (2019.01)
(Continued)

(52) U.S. Cl.
CPC ......... *G06F 21/6245* (2013.01); *G06F 16/00* (2019.01); *G06F 16/90335* (2019.01);
(Continued)

(58) Field of Classification Search
CPC ............... G06F 21/62; G06F 21/6245; G06F 16/90335; G06F 16/00; G06F 16/903;
(Continued)

(56) References Cited

U.S. PATENT DOCUMENTS 7,124,033 B2 * 10/2006 Hinds .................. C12Q 1/6827
702/19
7,668,658 B2 * 2/2010 Koster ................ C12Q 1/6827
435/6.11

(Continued)

FOREIGN PATENT DOCUMENTS

WO    2007084902 A2    7/2007
WO    2011067765 A1    6/2011

OTHER PUBLICATIONS

1000 Genomes Project Consortium, "An integrated map of genetic variation from 1,092 human genomes", Nov. 1, 2012, pp. 56-65, vol. 491, Publisher: Nature, Published in: doi:10.1038/nature11632.

(Continued)

*Primary Examiner* — Jayesh M Jhaveri
(74) *Attorney, Agent, or Firm* — Beusse Wolter Sanks & Maire; Eugene J. Molinelli

(57) ABSTRACT

Techniques to determine if an individual is a member of an ensemble contributing to combined genomic data include determining a site frequency spectrum (SFS) for alleles in the combined genomic data, and a number N of individuals contributing to the combined genomic data. Based on the SFS and N, both a number of queries NQ and a number of yeses NY are determined. NY is a number of yes responses to NQ queries, which indicates a particular likelihood that (Continued)

the individual is a member of the ensemble. Output is based on at least one of NQ and NY. For example, fewer than NQ queries from a single source are answered from a beacon. Alternatively, the likelihood that an individual is a member of the ensemble is determined based on responses to NQ queries about NQ different alleles present in the individual and NY.

21 Claims, 15 Drawing Sheets

(51) Int. Cl.
*G06F 16/903* (2019.01)
*G16B 20/00* (2019.01)
*G16B 50/00* (2019.01)
*G16B 20/40* (2019.01)
*G16H 10/60* (2018.01)

(52) U.S. Cl.
CPC ............ *G16B 20/00* (2019.02); *G16B 20/40* (2019.02); *G16B 50/00* (2019.02); *G16H 10/60* (2018.01)

(58) Field of Classification Search
CPC ........ G16H 10/60; G16B 20/00; G16B 20/40; G16B 50/00
See application file for complete search history.

(56) References Cited

U.S. PATENT DOCUMENTS

| | | | |
|---|---|---|---|
| 2003/0186280 A1 | 10/2003 | Kennedy | |
| 2005/0026117 A1* | 2/2005 | Judson | G06F 19/328 434/154 |
| 2008/0227063 A1* | 9/2008 | Kenedy | G16H 50/30 434/219 |
| 2008/0255768 A1* | 10/2008 | Martin | C12Q 1/6888 702/20 |
| 2012/0141450 A1* | 6/2012 | Salas Perez-Rasilla | C12Q 1/6883 424/94.3 |
| 2012/0329726 A1* | 12/2012 | Taguchi | C12Q 1/6876 514/20.7 |
| 2013/0090909 A1 | 4/2013 | Dudley et al. | |
| 2015/0078552 A1* | 3/2015 | Perlin | C12Q 1/6851 380/255 |

OTHER PUBLICATIONS

Clayton, David, "On inferring presence of an individual in a mixture: a Bayesian approach", May 19, 2010, pp. 661-673, vol. 11, No. Issue 4, Publisher: Biostatistics, Published in: doi:10.1093/biostatistics/kxq035.

Erlich, Yaniv et al., "Routes for breaching and protecting genetic privacy", Jun. 17, 2014, pp. 409-421, vol. 15, Publisher: Nature Reviews: Genetics, Published in: doi:10.1038/nrg3723.

Erlich, Yaniv et al., "Redefining genomic privacy: trust and empowerment", Nov. 2014, pp. 1-5, vol. 12, No. Issue 11 (e1001983), Publisher: PLOS Biology, Published in: http://repository.cshl.edu/30914/1/Witkowski%20PLoS%20Biology%202014.pdf.

The Genome of the Netherlands Consortium, "Whole-genome sequence variation, population structure and demographic history of the Dutch population", Jun. 29, 2014, pp. 818-825, vol. 46, Publisher: Nature Genetics, Published in: doi: 10.1038/ng.3021.

Goldstein, Benjamin et al., "Contemporary Considerations for Constructing a Genetic Risk Score: An Empirical Approach", Jul. 22, 2015, pp. 439-445, vol. 39, No. Issue 6, Publisher: Genetic Epidemiology, Published in: DOI 10.1002/gepi.21912.

Glusman, Gustavo et al., "Kaviar: an accessible system for testing SNV novelty", Sep. 28, 2011, pp. 3216-3217, vol. 27, No. 22 2011, Publisher: Bioinformatics, Published in: doi:10.1093/bioinformaticslbtr540.

Homer, Nils et al., "Resolving individuals contributing trace amounts of DNA to highly complex mixtures using high-density SNP genotyping microarrays", Aug. 29, 2008, pp. 1-9, vol. 4, No. Issue 8 (e1000167), Publisher: PLoS Genetics, Published in: doi:I0.1371/journal.pgen.1000167.

US, "International Search Report and Written Opinion for correspondence PCT Application PCT/US2016/055717", dated Dec. 23, 20116, pp. 1-9.

Jacobs, Kevin et al., "A new statistic and its power to infer membership in a genome-wide association study using genotype frequencies", Apr. 10, 2009, pp. 1253-1257, vol. 41, No. 11, Publisher: Nature Genetics, Published in: doi:I0.1038/ng.455.

Polderman, Tinca et al., "Meta-analysis of the heritability of human traits based on fifty years of twin studies", May 18, 2015, pp. 702-709, vol. 47, No. 7, Publisher Nature Genetics, Published in: doi: 10.1038/ng.3285.

Rothstein, Mark, "Putting the Genetic Information Nondiscrimination Act in context. Genetics in Medicine", Sep. 1, 2008, pp. 655-656, vol. 10, Publisher: Genetics in Medicine, Published in: https://doi.org/10.1097/GIM.0b013e31818337bd.

Sankararaman, Sriram, et al., "Genomic privacy and limits of individual detection in a pool", Aug. 23, 2009, pp. 965-967, vol. 41, No. 9, Publisher Nature Genetics, Published in: doi:I0.1038/ng.436.

Schrodi, Steven, et al., "Genetic-based prediction of disease traits: prediction is very difficult, especially about the future", Jun. 2, 2014, pp. 1-18, vol. 5, No. Article 162, Publisher: Frontiers in Genetics, Published in: doi: 10.3389/fgene.2014.00162.

Visscher, Peter, et al., "The limits of individual identification from sample allele frequencies: theory and statistical analysis", Oct. 2, 2009, pp. 1-6, vol. 5, No. Issue 10, Publisher: PLoS Genetics, Published in: https://doi.org/10.1371/journal.pgen.1000628.

Wei, Zhi, et al., "Large sample size, wide variant spectrum, and advanced machine-learning technique boost risk prediction for inflammatory bowel disease", Jul. 6, 2013, pp. 1008-1012, vol. 92, Publisher: American Journal of Human Genetics, Published in: https://doi.org/10.1016/j.ajhg.2013.05.002.

Wong, Lai-Ping, et al., "Deep Whole-Genome Sequencing of 100 Southeast Asian Malays", Jan. 10, 2013, pp. 52-66, vol. 92, Publisher: The American Journal of Human Genetics, Published in: http://dx.doi.org/10.1016/j.ajhg.2012.12.005.

Zerhouni, Elias, et al., "Protecting aggregate genomic data", "American Association for the Advancement of Science", Oct. 3, 2008, p. 44 vol. 322, No. 5898, Publisher: Science, Published in: https://www.jstor.org/stable/20144929.

ISA/EP, "International Search Report for the Patent application #US2016055717 dated May 9, 2019", pp. 1-14.

* cited by examiner

INDIVIDUAL
GENOMES

BEACON/
ENSEMBLE

FALSE POSITIVE

NQ

NQ

NQ

TECHNIQUES FOR DETERMINING WHETHER AN INDIVIDUAL IS INCLUDED IN ENSEMBLE GENOMIC DATA

CROSS-REFERENCE TO RELATED APPLICATIONS

This application is a 371 national stage application of PCT Application No. PCT/US16/55717, filed Oct. 6, 2016, which claims benefit of Provisional Appln. 62/238,386, filed Oct. 7, 2015, and Provisional Appln. 62/242,081, filed Oct. 15, 2015, the entire contents of each of which are hereby incorporated by reference as if fully set forth herein, under 35 U.S.C. § 119(e).

STATEMENT OF GOVERNMENTAL INTEREST

This invention was made with government support under Grant No. HG007436 awarded by the National Institutes of Health. The government has certain rights in the invention.

BACKGROUND OF THE INVENTION

Definitions

| | |
|---|---|
| allele | One of two or more forms of a gene or a genetic locus (generally a group of genes) on a single chromosome. |
| allele frequency | The rate of occurrence of a particular allele in an ensemble of individuals |
| ambiguous marker | A marker associated with heterozygous alleles or missing in a particular individual. |
| chromosome | A single piece of coiled DNA containing many genes, regulatory elements and other nucleotide sequences also containing DNA-bound proteins, which serve to package the DNA and control its functions. |
| diploid | Two homologous copies of each chromosome, with genes for the same characteristics at corresponding positions (loci), usually one from the mother and one from the father. |
| gene | A segment of DNA involved in producing a polypeptide chain. Specifically, a gene includes, without limitation, regions preceding and following the coding region, such as the promoter and 3'-untranslated region, respectively, as well as intervening sequences (introns) between individual coding segments (exons). |
| genotype | The genetic composition of an organism. |
| Genomic data | A list of alleles in the genotype of one or more individual organisms |
| haplotype | 1 - A combination of alleles (DNA sequences) at adjacent locations (loci) on the chromosome that are transmitted together. 2 - A set of single-nucleotide polymorphisms (SNPs) on a single chromosome of a chromosome pair that are statistically associated. |
| heterozygous | A diploid organism is heterozygous at a gene locus when its cells contain two different alleles of a gene. Heterozygous genotypes are represented by a capital letter (representing the dominant allele) and a lowercase letter (representing the recessive allele), such as "Rr" or "Ss". The capital letter is usually written first. |
| LD | Linkage disequilibrium, the non-random association of alleles at two or more loci, not necessarily on the same chromosome. |
| marker | A gene or unique DNA sequence with a known location on a chromosome that can be used to determine the chromosome location of an arbitrary sequenced portion of DNA. |
| nucleic acid | A molecule comprising a sequence of one or more repeating chemical units known as "nucleotides" or "bases" or "base pairs" (bp). There are four bases in deoxyribonucleic acid (DNA): adenine, thymine, cytosine, and guanine, represented by the letters A, T, C and G, respectively. In Ribonucleic acid (RNA) the base uracil (U) replaces the base thymine (T). |
| reference panel | A full set of haplotypes represented in a population, each haplotype represented by a set of SNPs at known positions relative to a set of markers along each chromosome. |
| phasing | Determining which alleles (indicated by the variant SNPs) exist together on the same chromosome, i.e., belong to the same haplotype. |
| protein | A generic term referring to native protein, fragments, peptides, or analogs of a polypeptide sequence. Synonyms used herein include "polypeptide." Hence, native protein, fragments, and analogs are species of a polypeptide genus. |
| sample | includes any biological specimen obtained from a subject |
| Site frequency spectrum | the number of different alleles relative to a reference genome in an ensemble of N individuals, which occur a given multiple of times for several different multiples from 1 to N − 1. |
| Site frequency spectrum, folded | the number of minor alleles in an ensemble of N individuals without a reference genome, which occur a given multiple of times for several different multiples from 1 to N/2. |
| SNP | Single-nucleotide polymorphism, a DNA sequence variation occurring when a single nucleotide in the genome (or other shared sequence) differs between members of a biological species or paired chromosomes in an individual. The vast majority of polymorphic sites are bi-allelic, meaning that no more than two possible distinct alleles can be observed at these sites. As used herein, a 0 indicates one nucleotide at the position of the SNP and a 1 indicates a different nucleotide. |

| | |
|---|---|
| Subject | An organism that is an object of a method or material, including mammals, e.g., humans, dogs, cows, horses, kangaroos, pigs, sheep, goats, cats, mice, rabbits, rats, and transgenic non-human animals as well as plants and protists. Synonyms used herein include "patient" and "animal". |
| Treating | Taking steps to obtain beneficial or desired results, including clinical results, such as alleviating or ameliorating one or more symptoms of a disease; diminishing the extent of disease; delaying or slowing disease progression; ameliorating and palliating or stabilizing a metric (statistic) of disease. "Treatment" refers to the steps taken. |

Most humans carry two copies of every chromosome in their genome—one inherited from the mother, the other from the father. Current genotyping and sequencing technologies have enabled the ability to rapidly and inexpensively discover the genotypes of an individual at a large number of sites in the genome (based on the SNPs in the vicinity of various markers).

Genotype information in the form of genomic data gives the occurrence of the alleles, e.g., the existence of multiple values for each of one or more of the SNPs. The human genetics community has provided for secure sharing of genomic data from patient participants in genetic research. Beacons are web servers that answer allele presence queries such as "Do you have a genome that has a specific nucleotide (e.g., A) at a specific genomic position (e.g., position 11272 on chromosome 1)?" with "Yes"/"No" responses.

SUMMARY OF THE INVENTION

In an ensemble of DNA sequence data from multiple individuals it is often the case that membership of the individual is unknown. For example, this information is hidden for published genomes called beacons for which the occurrence of different alleles in populations of a certain phenotype, e.g., Eastern Europeans or cancer patients, is available. As another example, forensic data collected at a crime scene may have samples with DNA from many contributors, such as victims, bystanders and perpetrators, resulting in another mix of alleles. Inventors have recognized that these ensembles can be penetrated to determine the likelihood that an individual, with at least some known alleles, is a member of the ensemble, even if allele frequency in the ensemble is not known. In various embodiments, these new techniques use a known or inferred site frequency spectrum to determine whether genomic data of an individual is included in ensemble genomic data, and thus whether the individual is a member of the ensemble.

In a first set of embodiments, a method includes obtaining first site frequency spectrum data that indicates a site frequency spectrum for alleles in first genomic data aggregated for an ensemble of unknown individuals. The method also includes determining a number N that indicates a number of individuals whose individual genomic data are aggregated in the first genomic data. The method further includes determining automatically on a processor, based on the first site frequency spectrum data and the number N, both a number NQ and a number NY, wherein the number NQ is a number of queries to employ, wherein each query requests whether a particular allele from an individual is present in the first genomic data, and the number NY is a number of yes responses that indicate a particular likelihood that the individual is a member of the ensemble. The method still further includes providing output based on at least one of NQ or NY.

In some embodiments, responses to one source of queries are provided only for fewer than NQ queries in a predetermined time interval, e.g., to protect individual identities in a beacon.

In other embodiments, the method further includes determining whether an individual subject is a member of the ensemble based on responses to the NQ queries and the value of NY. For example, NQ queries are submitted to a system that manages the first genomic data. In some of these embodiments, at least NQ alleles are selected at random from second genomic data determined for a sample collected from a particular individual subject. In these embodiments, submitting the queries includes submitting a query for each of the at least NQ alleles selected at random from the second genomic data. In some embodiments, the method includes accumulating a number of affirmative responses to the at least NQ queries and determining the likelihood that the particular individual subject is a member of the ensemble based on the number of affirmative responses and the threshold number NY. In some embodiments, the method includes presenting on a display device output data that indicates the likelihood that the particular individual is a member of the ensemble.

In other sets of embodiments, a computer-readable medium or a system is configured to perform one or more of the steps of one or more of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

A method and apparatus are described for determining likelihood that an individual is a member of an ensemble based on ensemble genomic data. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader rang around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described in the context of membership of an individual in a published beacon of genomic data. However, the invention is not limited to this context. In other embodiments, membership is determined for a forensic sample collected at the scene of an incident being investigated, where the individual is one of a prospective or suspected victim, a prospective or suspected bystander or witness, or a prospective or suspected perpetrator.

1. OVERVIEW

Figure 1:
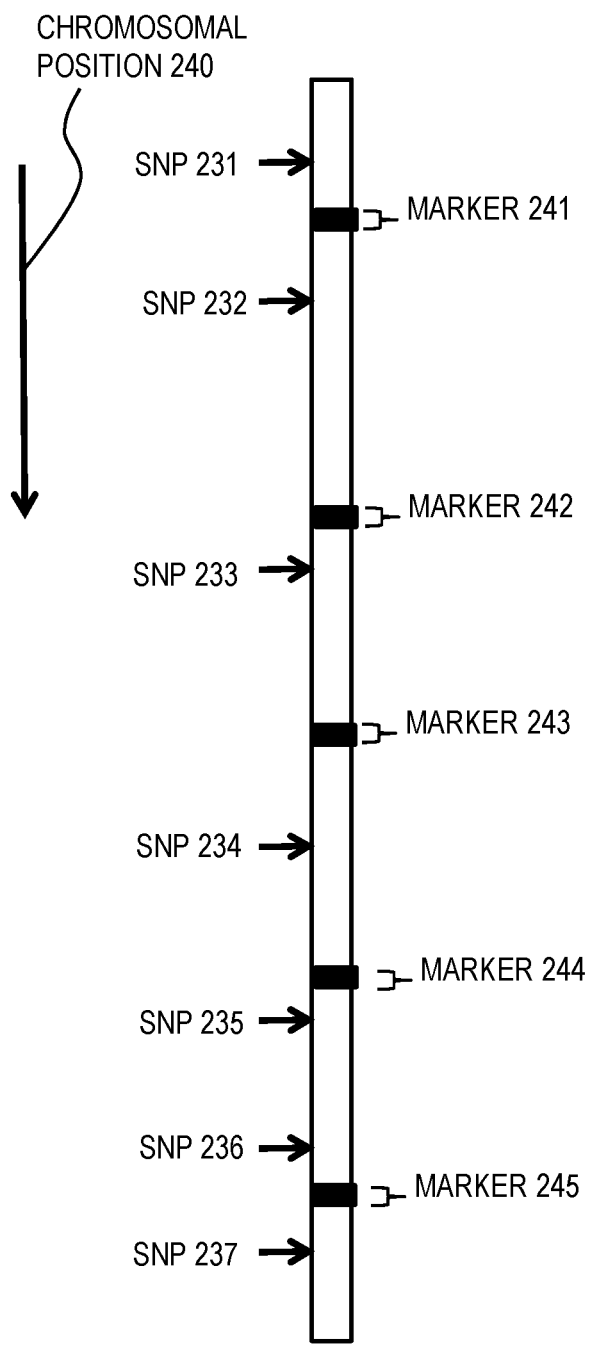
FIG. 1 is a block diagram that illustrates example markers and SNPs along a chromosome, according to an embodiment.

FIG. 1 is a block diagram that illustrates example markers 241, 242, 243, 244, 245 and SNPs 231, 232, 233, 234, 235, 236, 237 as alleles along a chromosome indicated by chromosomal position 240, according to an embodiment. The genomic data is a list of 0 s and 1 s, each representing the presence (1) or absence (0) of an allele in the individual.

A great deal of human genomic data will be collected in the context of health care, along with linked phenotypes in Electronic Health Records (EHRs). A major goal of the human genomics community is to enable efficient sharing, aggregation, and analysis of these data in order to understand the genetic contributors of health and disease. Previous large-scale data-sharing approaches have had limited success due to the potential for privacy breaches and risks of participants being re-identified. Homer (2008) and others (see, for example, Sankararaman, 2009; Jacobs, 2009; Visscher, 2009; and Clayton, 2010) showed that subjects in a genome-wide association study could be re-identified using allele-frequencies, resulting in the removal of publicly-available allele frequency data (see, e.g., Zerhouni, 2008). The Beacon Project by the Global Alliance for Genomics and Health aims to simplify data sharing through a web service ("beacon") that provides only allele presence information. Users can query institutional beacons for information about genomic data available at the institution. Queries are of the form "Do you have a genome that has a specific nucleotide (e.g., 'A') at a specific genomic position (e.g., position 11272 on chromosome 1)?" and the beacon server can answer "Yes" or "No". Beacons are intended to be easy to setup and to allow data sharing while protecting participant privacy. By providing only allele presence information, beacons are safe from re-identification attacks that require allele frequencies.

However, a privacy breach from a beacon would be troubling since beacons often summarize data having a particular disease of interest. For instance, identifying that a given genome is part of the SFARI beacon, which contains genomic data from families with a child having autism spectrum disorder, means that the individual belongs to a family where some family member has autism spectrum disorder. Thus, if beacons leak membership information, then they also leak phenotype information. While genetic privacy is protected to some extent by the Genetic Information Nondiscrimination Act (GINA), the offered protections are limited, and GINA does not apply for long term care insurance, life insurance, disability insurance and other special cases (Rothstein 2008). Therefore, data-sharing mechanisms such as beacons must protect participant privacy.

Figure 2A:
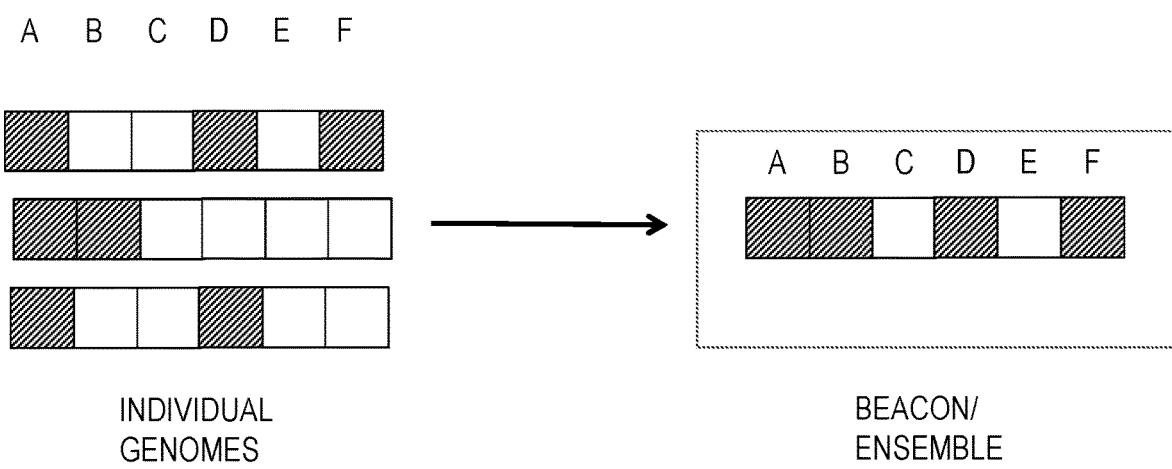
FIG. 2A is a block diagram that illustrates highly simplified example genomic data for an ensemble compared to genomic data of individuals in the ensemble, according to an embodiment.

In beacon genomic data, the details about the genomic data of contributing individuals is purposefully hidden. This is done by just indicating by a 1 any allele that is found in any member of the ensemble, and indicating by a zero an allele that is absent from every member of the ensemble. FIG. 2A is a block diagram that illustrates highly simplified example genomic data for an ensemble compared to genomic data of individuals in the ensemble, according to an embodiment. For simplicity each individual is represented by the state of six alleles, represented by boxes lettered A through F going left to right in the diagram. The presence of an allele is indicted by a shaded box to represent a 1 and a white box to represent a zero. The genomic data of three individuals are depicted. As can be seen, in the simple example, the first individual (top) has alleles A, D and F; the second (middle) has alleles A and B, and the third individual (bottom) has alleles A and D. No individual has alleles C or E. In a beacon data set, any allele that is found in any individual is marked with a one (shaded), but no information is given on how many times each allele occurs in the ensemble. Further, the beacon is not presented to users of the beacon in its entirety, but instead a user is required to indicate a single allele (by chromosome and position) and in response the beacon returns an affirmative (e.g., 1) if shaded, or negative (e.g., 0) if unshaded. Because the human genome includes many millions of alleles and any individual can have anywhere from about 3 million to about 5 million alleles present, it is tedious and time consuming to query a beacon for every allele. If the individual is a member of the ensemble, then every query of the individual's alleles should return a yes. If the genomic data of the individual and the beacon were without noise, a singe negative response would rule out membership of that individual in the ensemble. Because the genomic data can have noise, it is considered that one cannot be sure if an individual is a member of the ensemble that formed the beacon just because a few responses are negative.

Figure 2B:
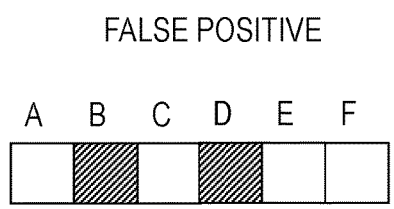
FIG. 2B is a block diagram that illustrates highly simplified example genomic data for an individual not part of the ensemble that might give a false positive for membership in the ensemble, according to an embodiment.

In fact, it is possible to come to a conclusion that an individual is a member of the beacon ensemble when the individual is not (a type II error also called a false positive error). FIG. 2B is a block diagram that illustrates highly simplified example genomic data for an individual not part of the ensemble that might give a false positive for membership in the ensemble, according to an embodiment. This individual has alleles B and D. Queries on both these alleles would return a positive response from the beacon. Yet the individual is not a member of the ensemble, i.e., is not one of the three individuals whose genomic data is depicted in FIG. 3A. Because the beacons can give such false positives, it is further considered that one cannot be sure if an individual is a member of the beacon.

Similarly, in a forensic sample that may have DNA from multiple persons at a scene, including one or more victims, bystanders or witnesses, and perpetrators, genomic data can be obtained for the ensemble of persons, as in a beacon. However, for similar reasons, knowledge of whether an individual, for whom genomic data is available in whole or in part, is a member of the ensemble is not certain. For simplicity herein, an ensemble refers to a collection of one or more individuals whose genomic data is combined in a beacon or simulation or by sequencing a forensic sample or experimental sample or other sample. Ensemble beacons or ensemble genomic data refers to genomic data based on the genomic data of the individuals in the ensemble even if combined as in beacons or forensic samples.

However, as demonstrated below for beacon data, if a site frequency spectrum (SFS, also called an allele frequency spectrum) is known or can be inferred, and if a number (N) of members of the ensemble is known or can be bracketed, and if a mismatch rate ($\delta$) for genomic data can be estimated or bracketed based on noise in obtaining genomic data for the individual and the ensemble, then a likelihood that an individual is a member of the ensemble can be determined based on the number of positive response received from a given number of queries. Furthermore, because relatives have similar alleles to an individual, the likelihood that a relative of the individual is included in the ensemble can also be determined based only on the genomic data for the individual.

Figure 3:
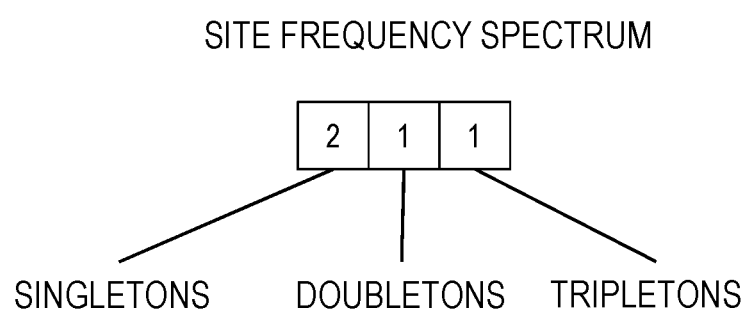
FIG. 3 is a block diagram that illustrates highly simplified example site frequency spectrum for an ensemble that is used to determine likelihood of membership, according to an embodiment.

The site frequency spectrum (SFS) does not give the frequency of a particular allele in the beacon data, but instead says how many alleles occur with a given frequency (e.g., how many alleles are singletons that occur once in the genomic data of the ensemble, how many alleles are doubletons that appear twice, etc.) FIG. 3 is a block diagram that illustrates highly simplified example site frequency spectrum for an ensemble that is used to determine likelihood of membership, according to an embodiment. Looking at the data in FIG. 2A, it is clear that allele A is a tripleton, allele B is a singleton, allele D is a doubleton and allele F is a singleton in the individual genomes. Thus there are two singletons, one doubleton and one tripleton. This is shown in FIG. 3, by the values (2, 1, 1) in the site frequency spectrum. Note that no specific allele information is provided. Thus a query is also needed for any specific allele.

The inventors have discovered how the site frequency spectrum provides information on the likelihood that enough queries have been advanced to determine whether an individual or family member of the individual is a member of the ensemble. Thus the likelihood of membership can be determined even without knowing frequency of individual alleles in the ensemble. This is an advantage in some embodiments, because while allele frequencies can vary greatly among ensembles, site frequency spectra have a tendency to be similar in ensembles from one species (e.g., all human ensembles). So even if a specific SFS is not known, one can be estimated from a similar population or for humans in general.

Note further that all members of the example ensemble have allele A. This is possible because alleles are defined relative to a reference sequence (e.g., the consensus human genome) independent of the ensemble, and not by differences that occur only within the ensemble. Otherwise, all members of the ensemble would have the same sequence at position A and that positon would not be considered an allele position. This also makes clear that, in an ensemble of N individuals, it is possible to have one or more alleles with a frequency of N. In some embodiments, alleles are defined within the ensemble and an allele can have no more than N−1 occurrences. If the most common version of the allele is considered normal (allele absent) then no allele can have more than N/2−1 occurrences.

As shown below for beacon data, by advancing enough queries almost any degree of certainty can be achieved in a statement about whether an individual belongs to an ensemble. For any degree of certainty desired, a number of queries and number of positive responses can be determined that will indicate membership with that degree of certainty.

Such a result has a disadvantage of exposing the individual as a member of the ensemble, e.g., an ensemble of persons with a particular phenotype, e.g., a disease or condition associated with the beacon, thus infringing on that individual's privacy. As a consequence, procedures for querying the beacon should be changed to compensate, e.g., by limiting the number of queries from any source, e.g., in a predetermined time period, such as one month, one year or all time. On the other hand, the same result offers the advantage of determining which remedial actions are sufficient. Such remedial actions are described below.

Furthermore, this same result has an advantage of determining whether an individual (e.g., suspect or victim) contributed to a sample mixing DNA from multiple persons, as in a forensic sample. As a result, a suspect can be placed at the scene where the sample was collected with a specified degree of likelihood.

Figure 4:
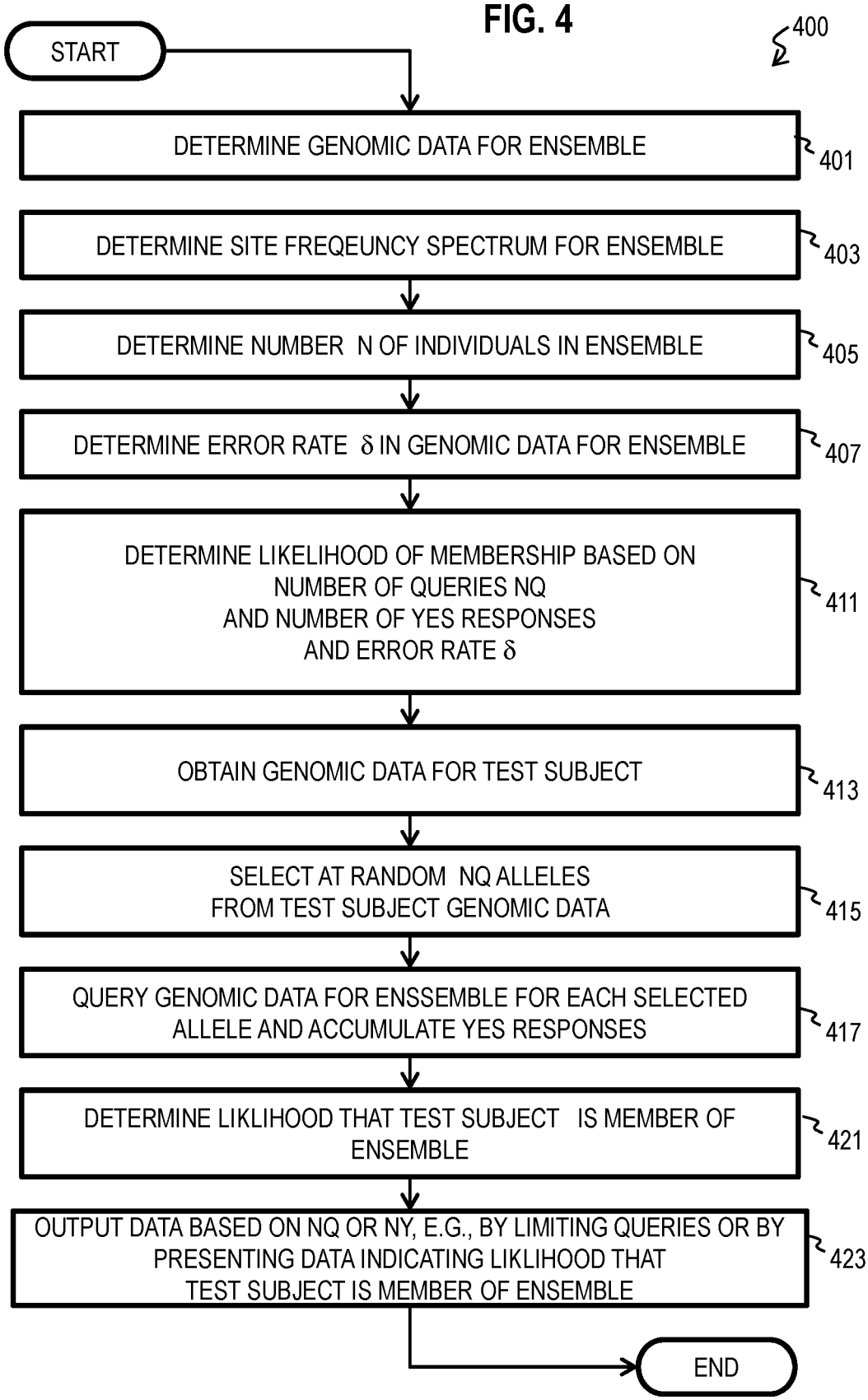
FIG. 4 is a flow diagram that illustrates an example method for determining likelihood that an individual is a member of an ensemble, according to an embodiment.

FIG. 4 is a flow diagram that illustrates an example method for determining likelihood that an individual is a member of an ensemble, according to an embodiment. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 401, a source of genomic data for an ensemble is identified. For example, a particular beacon is identified (such as the AMPlab, ICGC and NCBI beacons, among others, see tables below), or DNA sequencing of a forensic sample is obtained from a service or by use of an SNP micro array, or any other method known in the art at the time the method is implemented.

In step 403, a site frequency spectrum is determined for the ensemble. If one is published for the beacon, then that SFS is used. If not, then in some embodiments, the published SFS for a similar population, e.g., same ethnic composition, or similar medical condition, is used. In some embodiments, a SFS for the consensus human genome is used. Thus the approach is generalizable to many populations. In some embodiments, the SFS is parameterized by the values of two shape parameters a' and b' of a Beta distribution, as described in more detail below.

In step 405, a number of individuals in the ensemble is determined. In some embodiments, that number is given. In other embodiments, when the number N is not known, a conservative estimate of the number is made. The larger is the number of individuals in the ensemble, the more uncertain is the result. Thus a conservative estimate is a number reasonably expected to be greater than or equal to an unknown number of individuals in the ensemble.

In step 407 a mismatch rate ($\delta$) is determined for the ensemble genomic data. This is the probability that a query that should return an affirmative response instead returns a negative response. In various embodiments, the mismatch rate is published or estimated using any method known in the art at the time the method is implemented. The example embodiments below demonstrate some example ways to determine the mismatch rate. In some embodiments, the mismatch rate is assumed to be zero and step 407 is omitted.

In step 411, the number of different alleles to query (NQ) and the number of affirmative responses (NY) to achieve a certain degree of certainty (also called likelihood) in the membership result is determined based on the values for the SFS, N and $\delta$. Various ways to do this are derived in the example embodiments described below. For example test statistic A is computed as a difference or ratio of likelihoods for a null hypothesis that the individual is not a member of the ensemble and an alternate hypothesis that an individual is a member of the ensemble. For each query genome, the likelihood of the beacon responses to n allele presence queries is calculated under the null hypothesis $H_0$ (e.g., that a given individual or relative is not in the beacon) and again under an alternative hypothesis $H_1$ (e.g., that the given individual or a relative is in the beacon).

Two scenarios are considered, to show how this information yields insight into ensemble membership. In scenario 1, every SNP in the population is a singleton. If there are no sequencing errors, then the chance of false positive (i.e., chance of producing 1 at single SNP if G is not in B)=0. Every SNP will produce a 0 response on query (since G has the only alternate allele at the SNP of the query). In scenario 2, any SNP is a singleton with probability s (0≤s<1) and non-singleton with probability 1-s. The chance of a false positive (i.e., the chance of producing 1 at single SNP if G is not in B)=s×0+(1-s), which is the probability that someone else has the allele. The chance of all n returning a positive response is less than or equal to $(1-s)^n$. This value falls to zero quickly, for example $(0.9)^{200}=7\times10^{-10}$. So after enough queries the change for a false positive is small.

In some embodiments, the test statistic A is calculated as the ratio of the two likelihoods as given by Equation 4 below. In other embodiments another statistic is based on the two likelihoods. In some embodiments, the log likelihood is determined for the null hypothesis and the alternative hypothesis, and the two log likelihoods are compared. A determination is made of whether the alternative hypothesis is true is based on a comparison of the two likelihoods, e.g., by a difference or ratio. A relationship between the number of queries (required to achieve a desired power and false positive rate) and the number of individuals in the beacon is given by Equation 6 below for an individual. N represents the number of individuals in ensemble; n represents the number of queries. The number of yeses is represented by the sum of $x_i$'s, which are responses from the ensemble, encoded as $x_i=1$ for yes and $x_i=0$ for no. The relationship is given by Equation 9 below for a relative with degree of similarity given by the parameter $\phi$. A result of step 411 is a number of queries (NQ) that should be advanced to the beacon (equivalent to a number of alleles to identity in the forensic sample) to determine membership at a particular level of certainty (a certain statistical power). In the illustrated embodiments, the statistical power is a function of the false positive rate $\alpha$ that can be tolerated. Some assumptions and simplifications are made to derive the forms of the equations used in the illustrated embodiments. In other embodiments, other assumptions or simplifications are made instead of or in addition to those made in the examples described below.

In step 413, genomic data is determined for an individual test subject, e.g., from a record on file or from a DNA sequencing service from a sample drawn from the individual test subject, including results from a SNP micro array. The number of alleles identified in the individual should be at least the number of queries (NQ) to determine membership at the desired level of certainty and preferably many times that number.

In step 415, a number NQ of alleles are selected at random. There is no need to require that the selected alleles be singletons or have any other particular frequency. In some embodiments, however, only the most rare SNPs in a population that are also present in the individual are selected.

In step 417, it is determined how many of the selected alleles from the individual are present in the ensemble (e.g., how many positive responses are received from the beacon or how many of the selected alleles are listed in the genomic data for the forensic sample).

In step 421, the likelihood that the test subject is a member of the ensemble is determined. For example, if the number of yes responses from the beacon (or alleles found in the forensic sample) are at or greater than the threshold number NY determined in step 411, then it is determined that the test subject is a member of the ensemble at the level of certainly associated with the threshold.

In step 423 output data is presented based on NQ or NY. For example, in some embodiments, output indicating the likelihood is presented on a display device, such as display 514 described below with reference to FIG. 5. In some embodiments, treatment of the test subject is based at least in part on the output. For example, if the test subject is a member of an ensemble that has a certain disease or responds to a certain treatment, then the test subject is diagnosed with that disease or given that certain treatment.

In some embodiments, the method 400 is executed on the beacon side, e.g., at a server that provides the beacon service, and steps 413 through 421 are omitted. In these embodiments, step 423 includes limiting the number of queries from any one source or user identifier to a number less than NQ associated with a certainty of about 50%, or selected in a range from about 20% to about 50%. In some embodiments, the limit on number of queries accepted from a single source is enforced for a predetermined time interval or period, e.g., for one week or one month or one year or for all time. In some embodiments, the responses are censored and a query for an SNP associated with a rare allele is indicated to be absent in the response, even if it is present in the ensemble.

Thus, these techniques allow robust identification of individuals from DNA mixtures (e.g., using SNP microarray data) for many populations in a way that is independent of the actual frequency of each individual allele, or prevent or inhibit unintentional identification of an individual as a member of an ensemble, such as a beacon.

2. EXAMPLE EMBODIMENTS

Here is shown, by various example embodiments, that individuals in a beacon are susceptible to re-identification even if the only data shared is "presence"/"absence" information about alleles in a beacon. Specifically, a likelihood ratio test is demonstrated that indicates whether a given individual is present in a given genetic beacon. This test is not dependent on individual allele frequencies and is the most powerful test for a specified false positive rate. Through simulations, it is shown that in a beacon with 1,000 individuals, re-identification is possible with just 5,000 queries. Relatives can also be identified in the beacon. Re-identification is possible even in the presence of sequencing errors and variant calling differences. In a beacon constructed using 65 European individuals from the 1000 Genomes Project, it is demonstrated that re-identification is possible with just 250 SNP queries. With just 1000 SNP queries, it was possible to detect the presence of an individual from the Personal Genome Project (PGP) in an existing beacon. These results show that beacons can disclose membership and phenotypic information about participants and may not adequately protect privacy. Risk mitigation is proposed for some embodiments through policies and standards such as not allowing anonymous pings of genetic beacons, limiting a number of queries from a single source in a predetermined time period, or requiring minimum beacon sizes, among others, or some combination.

2.1 Bi-Allelic SNPs in Beacon Comprised of Unrelated Individuals from a Single Population Only bi-allelic single-nucleotide polymorphisms (SNPs) are considered in the following analysis. In response to a query q={C, P, A}, the beacon sends a response message with a value "Yes" (represented by the numerical value 1) if allele A is an alternate allele at position P on chromosome C with non-zero frequency in the samples used to construct the beacon, and answers "No" (represented by the numerical value 0) otherwise. Given a set of n queries Q={$q_1, \ldots, q_n$}, the beacon returns a set of responses R={$x_1, \ldots, x_n$}. In this example, it is assumed that the attacker has access to more information—the number of individuals in the beacon database N and the site frequency spectrum (SFS) of the population in the beacon, the latter parameterized as a Beta distribution with shape parameters (a', b').

Figure 7:
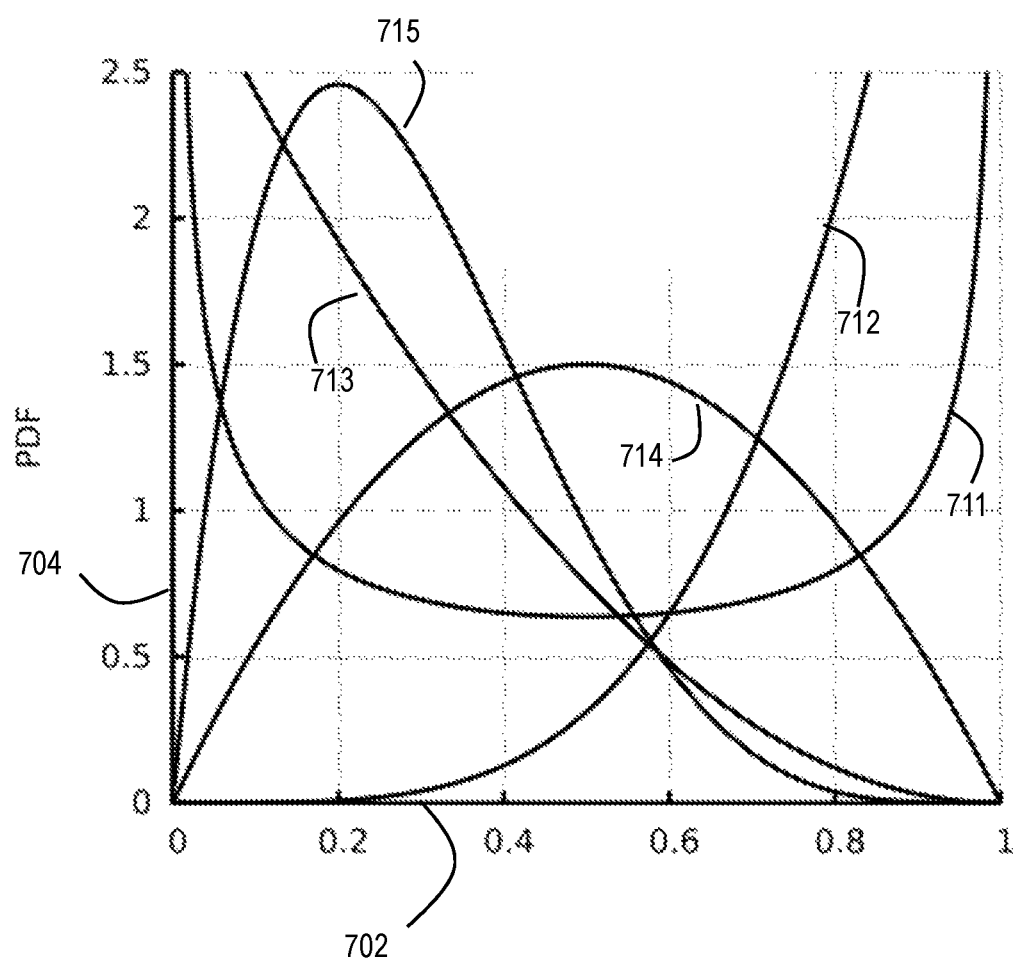
FIG. 7 is a graph that depicts the dependence of the beta function, used to describe a site frequency spectrum (SFS), on two shape parameters, according to an embodiment.

The Beta distribution is a continuous probability distribution, and has been applied to model the behavior of random variables limited to intervals of finite length in a wide variety of disciplines. For example, it has been used as a statistical description of allele frequencies in population genetics. Thus, it is assumed that alternate allele frequencies f for all SNPs observed in the population are distributed as f~Beta(a', b'). This is justified, for example, by Sankararaman 2009 or Clayton 2010. The Beta distribution for a probability density function (PDF) for a random variable r on the interval 0 to 1 is given by Equation 1.

$$\text{Beta}(r; a', b') = r^{a'-1}(1-r)^{b'-1}/B(a', b') \quad (1)$$

where B(a', b') is a function of a' and b' selected to ensure the probability integrates to 1 on the interval 0 to 1 and so is constant as r varies over the interval 0 to 1. FIG. 7 is a graph that depicts the dependence of the Beta function used to describe a site frequency spectrum (SFS) on two shape parameters, according to an embodiment. The horizontal axis indicates the value of a normalized independent variable, such as copy number for an allele normalized by the number of copies in an ensemble, and the vertical axis indicates the probability of that value. The distribution can be shaped to fit suitable empirical data, such as an SFS that indicates the distribution of allele copies in an ensemble of subjects, based on the two shape parameters a', b'. Five example shapes are represented by: trace 711 for a'=b'=0.5; trace 712 for a'=5, b'=1; trace 713 for a'=1, b'=3; trace 714 for a'=2, b'=2; and, trace 715 for a'=2, b'=5.

For this example attack scenario, a situation identical to that used by Homer et al. [1] and others is assumed, wherein the attacker receives a Variant Call Format (VCF) file for the query genome (the genome of the individual whose membership in the ensemble is at question) listing all the SNP positions in the query genome at which the individual has an alternate allele than the reference genotype calls for at the corresponding positions. The attacker then queries the beacon for all heterozygous positions using the alternate allele listed in the VCF and obtains the set of responses R from the beacon. If the query individual is present in the beacon, then every allele in the query genome must be present in the beacon. Thus the beacon will return a "Yes (1)" response to every query. If a query individual is not present in the beacon, then the beacon response will be "Yes (1)" if some individual in the beacon has the allele and "No (0)" otherwise.

Here is demonstrated a likelihood ratio test (LRT) that uses the responses R to decide whether the query genome is in the beacon or not. By calculating the likelihood of the responses, the method can differentiate query genome of individuals who are in the beacon from the query genome of individuals who are not in the beacon. This approach for re-identifying individuals within a beacon is based on a likelihood ratio test that uses the response information. For each query genome, the likelihood of the beacon responses to n allele presence queries is calculated under the null hypothesis $H_0$ that a given individual is not in the beacon and again under the alternative hypothesis $H_1$ that the given individual is in the beacon. A test statistic $\Lambda$ is calculated as the ratio of the two likelihoods.

To make this likelihood ratio test generalizable across populations, direct dependence on frequencies of specific alleles is removed since frequencies can vary considerably for a given allele across populations. Instead, this test is formulated to depend on the shape of SFS, which is described by (a', b'), the shape parameters of the Beta distribution. While allele frequencies for a given allele can vary considerably across populations, the SFS parameters for most populations are similar to each other as shown in Table 1. Only the genome based on an Affymetrix array of SNPs has considerably different shape parameters from the other populations.

TABLE 1

Beta distribution shape parameters estimated from site frequency spectra for simulation data and some public whole-genome datasets.

| Dataset | Number of samples | Estimated a' | Estimated b' |
|---|---|---|---|
| Simulation | 1000 | 0.1300 | 1.1300 |
| SSMP | 100 | 0.1848 | 0.8500 |
| GoNL | 498 | 0.1131 | 0.8574 |
| 1000 Genomes Phase 1 | 1092 | 0.0735 | 1.0096 |
| 1000 Genomes Phase 1 Affymetrix array | 1074 | 0.6483 | 1.2876 |

Therefore the results from a test that depends on the shape of the SFS but is independent of the actual frequencies of individual alleles can be generalized to many populations, e.g., using shape parameters of a' about 0.1 and b' about 1.0 for human genome datasets of unknown allele frequencies and unknown SFS. The shape of such a distribution would be expected to be something like a trace 713 of FIG. 7 for which the magnitude of b' is several times the magnitude of a'.

The shape parameters for the genome datasets in Table 1 were computed based on the frequency $f_i$ of each allele i among N individuals as follows. Note that each fi is the count of the number of times allele i occurs divided by N or 2N, depending on the type of frequency distribution used, so all the values occur on the interval between 0 and 1. Alternate allele frequencies for populations were modeled by Beta distributions similar to the approaches used by [2, 5]. If {f1, ..., fn} are distributed over the interval 0 to 1 as Beta(a', b'), and the sample mean $\bar{f}$ and sample variance $\bar{v}$ are defined as usual by Equation 2 and Equation 3, respectively.

$$\bar{f} = \frac{\sum_{i=1}^{n} f_i}{n} \quad (2)$$

$$\bar{v} = \frac{\sum_{i=1}^{n} (f_i - \bar{f})}{n-1} \quad (3)$$

then, the shape parameters a' and b' are deduced using the method of moments estimators and given by Equations 4 and 5.

$$a' = \bar{f}\left(\frac{\bar{f}(1-\bar{f})}{\bar{v}} - 1\right) \quad (4)$$

$$b' = (1-\bar{f})\left(\frac{\bar{f}(1-\bar{f})}{\bar{v}} - 1\right) \quad (5)$$

provided that $\bar{v} < \bar{f}(1-\bar{f})$.

In an ideal setting, one would expect responses $x_1 = x_2 \ldots = x_n = 1$ if a query genome g is in the beacon B. In practice, due to sequencing errors and differences in variant calling pipelines, there might be some mismatches between the query copy of a genome and its copy in the beacon. The mismatch happens with probability δ. Also there is a possibility of a false positive, where all the alleles in the query genome are in the beacon but the genome itself is not, as demonstrated above with reference to FIG. 2B.

Let the alternate allele frequency at the SNP corresponding to query $q_i$ be $f_i$. Since the beacon is only queried at the positions where the query genome is heterozygous, it is not a random sample of the beacon; and, thus $f_i$ is not distributed as Beta (a', b') but shows an ascertainment bias. In theory, $f_i \sim $ Beta (a, b), with a=a'+1 and b=b'+1, is the posterior distribution of the alternate allele frequency fat heterozygous sites, assuming Hardy-Weinberg equilibrium. Since the claimed method does not depend on the derivation, the derivation of the distribution for the query results is not repeated here. The derivation is incorporated by reference to the provisional application, as cited above. In practice, for both simulated and real genomic data demonstrated below, the observed values of the parameters of the posterior distribution are slightly different from their expectations given the distribution in the genome. In the power curves demonstrating likelihood described below, the correct estimated values of the parameters a and b for the simulated data are used rather than the theoretical expectation or estimates from real data.

The log-likelihood L(R) of a response set $R=\{x_1, \ldots, x_n\}$ can be written as Equation 6.

$$L(R) = \sum_{i=1}^{n} x_i \log[P(x_i=1)] + (1-x_i)\log[P(x_i=0)] \quad (6).$$

for each $x_i$ having two possible outcomes: true(1), e.g., the allele is present in the ensemble, or false (0), the allele is not present in the ensemble. The probability P of the outcome depends on the hypothesis. In various embodiments, the log likelihood is determined for a null hypothesis (e.g., the test subject or relative is not a member of the ensemble) and one alternative hypothesis (the test subject or relative is a member of the ensemble and $x_i=1$ for all i, or some other condition of interest), and the two log likelihoods are compared. A determination is made of whether the alternative hypothesis is true based on a comparison of the two likelihoods, e.g., by a difference or ratio. In this illustrated embodiment, a ratio of the two likelihoods is determined.

In this example embodiment, the null hypothesis is that the test subject (query genome) is not in the ensemble and the alternative hypothesis is that the test subject is in the ensemble. Under this alternative hypothesis, H1, the log likelihood is computed as given by equation (7)

$$L_{H1}(R) = \sum_{i=1}^{n} x_i \log[1-\delta D_{N-1}] + (1-x_i)\log[D_{N-1}] \quad (7)$$

Where $D_{N-1}$ is the probability that none of N−1 genomes in the ensemble has an alternative allele at a given position, which can be determined from the SFS. The example embodiment uses Equation 7 and the derivation of Equation 7 is not needed to practice the embodiment; therefore the derivation of Equation 7 is not repeated here. The derivation is incorporated by reference to the provisional application, as cited above.

Similarly, the log-likelihood under the null hypothesis H0 that the test subject (query genome) is not in the ensemble is computed as given by Equation 8.

$$L_{H0}(R) = \sum_{i=1}^{N} x_i \log[1-D_N] + (1 x_i)\log[D_N] \quad (8)$$

Where $D_N$ is the probability that none of N genomes in the ensemble has an alternative allele at a given position, again determined from the SFS. Again, this example embodiment uses Equation 8 and the derivation of Equation 8 is not needed to practice the embodiment; therefore the derivation of Equation 8 is not repeated here. The derivation is incorporated by reference to the provisional application, as cited above.

In this embodiment, the value of $D_N$ and $D_{N-1}$ are determined as follows. $D_N$ is defined as the probability that none of N individuals have an alternative allele. Thus $$D_N = \prod_{r=0}^{2N-1} \frac{b+r}{b+a+r} \quad (9a)$$

Recall, a and b are the parameters of the SFS distribution of the alternate allele frequency f at heterozygous sites. In this embodiment, equation 9a is evaluated using the Gamma function, Γ. The gamma function is the well known extension of the factorial function to real and complex numbers, so in the case of a positive integer m, $\Gamma(m)=(m-1)!$. For complex number t with a positive real part, $G(t)=\int_0^\infty x^{t-1} e^{-x} dx$. The Stirling approximation to the Gamma function is used and is given by Equation 9b.

$$\Gamma(t) \approx \sqrt{\frac{2\pi}{t}} \left(\frac{t}{e}\right)^t \quad (9b)$$

Also used is the result that $$\lim_{y \to \infty} \left(1 - \frac{1}{y}\right)^y \approx \frac{1}{e} \quad (9c)$$

It is further assumed that N>>a, b and N>>1, so that $$\frac{a}{b+2N} << 1.$$

This leads to the estimate used herein for $D_N$, given by equation 9d $$D_N \approx \frac{\Gamma(a+b)}{\Gamma(b)(a+b+2N)^a} \quad (9d)$$

This example embodiment uses Equation 9d, and the derivation of Equation 9d is not needed to practice the embodiment; therefore the derivation of Equation 9d is not repeated here. The derivation is incorporated by reference to the provisional application, as cited above.

$D_{N-1}$ is defined as the probability that none of N−1 individuals have an alternative allele. Thus $$D_{N-1} = \prod_{r=0}^{2N-3} \frac{b+r}{b+a+r} \quad (10)$$

This can be approximated with Equation 9d by replacing N in Equation 9d with (N−1).

The test statistic A in this embodiment is based on a log of the ratio of the likelihoods of the two hypotheses, and therefore is based on the difference of the log likelihoods, as given by Equation 11a.

$$A = L_{H0}(R) - L_{H1}(R) \quad (11a)$$

which, after substituting Equation 8 for the first term and Equation 7 for the second term, yields $$\Lambda = nB + C \sum_{i=1}^{n} x_i \quad (11b)$$

where $$B = \log\left[\frac{D_N}{\delta D_{N-1}}\right] \quad (11c)$$

$$C = \log\left[\frac{\delta D_{N-1}(1-D_N)}{D_N(1-\delta D_{N-1})}\right] \quad (11d)$$

Again, this example embodiment uses Equation 11b through 11d, and the derivation of Equations 11b through 11d is not needed to practice the embodiment; therefore the derivation of Equations 11b through 11d is not repeated here. The derivation is incorporated by reference to the provisional application, as cited above.

An advantage of Equation 11b is that it is understood to be a test for a simple null hypothesis, $H_0$, that has probability $\theta = 1 - D_N$ of a consistent result against a simple alternative hypothesis H1, that has a probability $\theta = 1 - \delta D_{N-1}$ of a consistent result when one is given R samples as a Bernoulli random variable, $x_i \sim \text{Bernoulli}(\theta)$, that is, $x_i$ is a random variable with only two possible outcomes, true (1) that the allele at positon i is in the ensemble, or false (0), it is not, as described above. The $x_i$ (whether an allele is present in the ensemble) can only take two values: 1 (present) or 0 (absent). So each $x_i$ is a Bernoulli random variable by definition. Each $x_i$ has the same $\text{Prob}(x_i=1)$ because in the absence of frequency information, all alleles are similar in that they are generated from the SFS. Therefore the $x_i$ are assumed to be independent and identically distributed (i.i.d.). By the Neyman-Pearson lemma, the likelihood ratio test, 11b, is the most powerful test for a given test size. The size of a test in hypothesis testing literature is defined as the probability of falsely rejecting the null hypothesis (e.g., falsely claiming an allele is present in the beacon when it is in fact absent). So the test size can be considered to be the (expected) false positive rate when the null hypothesis is true, given by a false positive rate, α.

In this embodiment, the null hypothesis is rejected if the likelihood is much less than the likelihood of the alternative.

This is expressed in terms of $\Lambda<t$ for some threshold t. The threshold is selected to meet some arbitrary false positive rate, $\alpha$, e.g., a false positive rate of 1% or 5%. Thus a threshold $t_\alpha$ associated with a given false positive rate $\alpha$ is one such that the test statistic $\Lambda$ will be less than that threshold, $t_\alpha$, with a probability of $\alpha$, as given by Equation 12.

$$P(\Lambda<t_\alpha|H_0)=\alpha. \tag{12}$$

This is equivalent to rejecting the null hypothesis under the conditions of Expression 13a and Equation 13b.

$$\Sigma_{i=1}^n x_i > t'_\alpha \tag{13a}$$

That is, the null hypothesis is rejected if the number of yeses is greater than a normalized threshold $t'_\alpha$, where $$t'_\alpha = \frac{t_\alpha - nB}{C} \tag{13b}$$

Again, this example embodiment uses Equations 13a and 13b, and the derivation of Equations 13a and 13b is not needed to practice the embodiment; therefore the derivation of Equations 13a and 13b is not repeated here. The derivation is incorporated by reference to the provisional application, as cited above. In this embodiment, the normalized threshold $t'_\alpha$ serves as the number NY that is a number of yes responses that indicate a particular likelihood (particular false positive rate, $\alpha$) that the individual is a member of the ensemble.

The likelihood that the conclusion is correct, $1-\beta$, is called the power of the test, where $\beta$ is the probability that the conclusion is erroneous. The power can be estimated as follows. Because the $x_i$ are Bernoulli random variables with known estimates of probabilities $\theta$ under the various hypotheses, the binomial distribution properties can be used to compare the distributions and estimate the power of the test of Equations 13a and 13b. The $x_i$ are independent and identically distributed under each hypothesis, therefore the number of yeses ($\Sigma_{i=1}^n x_i$) expected under each hypothesis is given by the Binomial distribution. For example, in this illustrated embodiment the number of yesses expected is given by Binomial(n, 1-$D_N$) for the null hypothesis and Binomial(n, 1-$\delta D_{N-1}$) for the alternate hypothesis. Therefore the power of the test is given by Equation 13c.

$$1-\beta=P(\Sigma_{i=1}^n x_i < t'_\alpha|H_1) \tag{13c}$$

The number of yeses that exceed the normalized threshold, $t'_\alpha$, given the alternate hypothesis is the test statistic. Note that the normalized threshold $t'_\alpha$, is defined in terms of the number of yeses that achieve a certain false positive rate for the null hypothesis in Equation 13b. A sufficient statistic for the likelihood ratio test is the number of "Yes" responses from the beacon.

To achieve any particular small value of $\alpha$, with the power of $1-\beta$, the number of queries, n, may have to be increased to get a useful result. In this illustrated embodiments, a suitable number of queries, NQ, is determined as follows.

In the null and alternative hypotheses, as stated above, $x_i$ is a Bernoulli random variable. Therefore, by the central limit theorem, the likelihood ratio test (LRT) statistic A has a Gaussian distribution. The parameters of the Gaussian distribution can be used to obtain a relationship between the number, n, of queries (required to achieve a desired power, $1-\beta$, and false positive rate, $\alpha$) and the number, N, of individuals in the beacon.

Let $\mu_0$ and $\sigma_0$ be the mean and standard deviation of the LRT statistic under the null hypothesis and $\mu_1$ and $\sigma_1$ be the corresponding values under the alternative hypothesis. For an LRT statistic that has a normal distribution the two distributions are related as follows $$\mu_0+\sigma_0 z_\alpha=\mu_1+\sigma_1 z_{1-\beta} \tag{14}$$

where the notation $z_y$ indicates the y-quantile of the standard normal distribution. For A described above, it can be shown that the value of n sufficient to achieve a particular power $(1-\beta)$ and false positive rate $(\alpha)$ is related to the number of genomes in the ensemble N by Equation 15.

$$\frac{n}{N^{a'+1}} = \frac{(z_\alpha - z_{1-\beta}\sqrt{\delta})^2 \Gamma(b'+1) 2^{a'+1}}{\Gamma(a'+b'+2)} \tag{15}$$

where a' and b' are the parameters of the Beta distribution used to fit the SFS, as described above; and, $\Gamma$ is the gamma function. This example embodiment uses Equation 15, and the derivation of Equation 15 is not needed to practice the embodiment; therefore the derivation of Equation 15 is not repeated here. The derivation is incorporated by reference to the provisional application, as cited above. Note that the right hand side of Equation 15 is independent of both n and N and depends on both the false positive rate $\alpha$ and the power $1-\beta$. Thus the value of n to achieve such power and rate increases is NQ; and, by virtue of Equation 15, NQ is proportional to the denominator of the left side of Equation 15, which is $N^{a'+1}$.

Therefore, in this embodiment, equations 15 and 13b provide the values for NQ and NY, respectively, in step 411.

Thus, a sufficient statistic for the likelihood ratio test is NY, the number of "Yes" responses from the beacon. If a "truth set" of individuals known to be (or not be) in the beacon is available, the critical value and power of the test can be computed using only the number of "Yes" responses from the beacon. Thus the empirical power is not dependent on the SFS parameters, which suggests the test is robust to SFS parameters.

2.2 Detecting Relatives

The relatedness of two individuals can be parameterized using a single parameter $\phi$ which is the probability that the two individuals share an allele at a single SNP. Thus, identical twins have $\phi=1$, parent-offspring and sibling pairs have $\phi=0.5$, first cousins have $\phi=0.25$ and so on.

Under the alternate hypothesis (a relative of the query genome g with relatedness $\phi$ is present in beacon B), the response $x_i$ is given by $x_i=0$ if none of the other N-1 genomes in the beacon has the alternate allele and (a) there is no mismatch between the query genome and its copy in the beacon and the relative is homozygous reference at the SNP, or (b) there is a mismatch between the query genome and its copy in the beacon and the relative is not homozygous reference at the SNP. Otherwise, $x_i=1$. For an individual that is heterozygous at a SNP with alternate allele frequency f, the genotype probabilities for a relative with relatedness $\phi$ can be determined given the genotype of the individual.

The likelihood for the null hypothesis remains the same as before. Under the alternate hypothesis (a relative of the query genome g with relatedness $\phi$ is present in beacon B), the log-likelihood is given by Equations 16a through 16c.

$$P(x_i = 0 \mid H_1) = \delta D_{N-1} + (1-2\delta)(1-\phi)^2 D_N + (1-2\delta)\phi(1-\phi)D_{N-\frac{1}{2}} \quad (16a)$$

where $$D_{N-\frac{1}{2}}$$

is estimated using Equation 9d by replacing N with the value N−½, and $$P(x_i = 1 \mid H_1) = 1 - \delta D_{N-1} - (1-2\delta)(1-\phi)^2 D_N - (1-2\delta)\phi(1-\phi)D_{N-\frac{1}{2}} \quad (16b)$$

Thus $$L_{H_1}(R) = \sum_{i=1}^{n} \left[ x_i \log\left\{1 - \delta D_{N-1} - (1-2\delta)(1-\phi)^2 D_N - (1-2\delta)\phi(1-\phi)D_{N-\frac{1}{2}}\right\} + (1-x_i)\log\left\{\delta D_{N-1} + (1-2\delta)(1-\phi)^2 D_N + (1-2\delta)\phi(1-\phi)D_{N-\frac{1}{2}}\right\} \right] \quad (16c)$$

This example embodiment uses Equations 16a through 16c, and the derivation of Equations 16a through 16c is not needed to practice the embodiment; therefore the derivation of Equations 16a through 16c is not repeated here. The derivation is incorporated by reference to the provisional application, as cited above.

The LRT statistic is calculated using the expressions of Equations 16a through 16c. Here the exact test uses the NY ($\Sigma_{i=1}^{n} x_i$) as the sufficient statistic (as before) and the sufficient statistic is binomially distributed under both hypotheses. The distribution of the null hypothesis is the same as before, the distribution of the alternate hypothesis $H_1$ is given by Equation 16d $\Sigma_{i=1}^{n} x_i \mid H_1$ is distributed as Binomial $\left(n, 1 - \delta D_{N-1} - (1-2\delta)(1-\phi)^2 D_N - (1-2\delta)\phi(1-\phi)D_{N-\frac{1}{2}}\right)$ (16d)

2.3 Censoring Output

It is valuable to determine how beacons should be modified in some embodiments to protect against such attacks as described above. In some embodiments, the beacon is modified based on the NQ or NY that are useful to re-identify an individual in the beacon. Because the rare alleles with low frequency in the SFS provide the most information about an individual, in a censoring approach, a YES response is not returned for queries for the rare SNPs. That is, one solution to the re-identification problem is to return accurate responses only for common variants. Thus, a setting is considered in which the beacon chooses a threshold frequency f* and returns "No" responses to queries for alleles that have frequency less than or equal to f* in the population (not necessarily in the beacon samples). For alleles at frequency larger than f*, the beacon will return an accurate response.

In this embodiment, under the alternative hypothesis (query genome g is present in beacon B, g ∈ B), the response $x_i$ is given by $x_i=0$ if either: (a) frequency of the allele $f_i \leq f^*$; or, (b) frequency of the allele $f_i > f^*$; and there is a mismatch between the query genome and its copy in the beacon and none of the other N−1 genomes in the beacon has the alternate allele. Otherwise, $x_i=1$.

The probability of a false result given the alternate hypothesis is given by Equation 17a through 17a through 17c.

$$P(x_i=0 \mid H_1) = \int_{f_i=0}^{f^*} P(f_i) df_i + \int_{f_i=f^*}^{1} \delta P(\text{no other of } N-1 \text{ genome has alternate} \mid f_i) P(f_i) df_i \quad (17a)$$

Which can be reduced to $$P(x_i=0 \mid H_1) = E_{N-1} \quad (17b)$$

where $$E_{N-1} = I_{f^*}(a,b) + \delta D_{N-1}\{1 - I_{f^*}(a,b+2N-2)\} \quad (17c)$$

Here $I_y(a,b)$ is the cumulative distribution function for a Beta distribution with shape parameters a and b at value y. This example embodiment uses Equations 17a through 17c, and the derivation of Equations 17a through 17c is not needed to practice the embodiment; therefore the derivation of Equations 17a through 17c is not repeated here. The derivation is incorporated by reference to the provisional application, as cited above Thus the log likelihood of the alternative hypothesis is given by Equation 18.

$$L_{H_1}(R) = \Sigma_{i=1}^{n} x_i \log(1 - E_{N-1}) + (1-x_i)\log(E_{N-1}) \quad (18)$$

Under the null hypothesis (query genome g is not in beacon B, g ∉ B), the response $x_i$ is given by $x_i=0$ if either: (a) frequency of the allele $f_i \leq f^*$; or, (b) frequency of the allele $f_i > f^*$; and none of the other N genomes in the beacon has the alternate allele. Otherwise, $x_i=1$.

The probability of a false result given the alternate hypothesis is given by Equation 17a through 19a through 19c.

$$P(x_i=0 \mid H_0) = \int_{f_i=0}^{f^*} P(f_i) df_i + \int_{f_i=f^*}^{1} \delta P(\text{no other of } N \text{ genomes has alternate} \mid f_i) P(f_i) df_i \quad (19a)$$

Which can be reduced to $$P(x_i=0 \mid H_0) = F_N \quad (19b)$$

where $$F_N = I_{f^*}(a,b) + D_N\{1 - I_{f^*}(a,b+2N)\} \quad (19c)$$

This example embodiment uses Equations 19a through 19c, and the derivation of Equations 19a through 19c is not needed to practice the embodiment; therefore the derivation of Equations 19a through 19c is not repeated here. The derivation is incorporated by reference to the provisional application, as cited above.

Thus the log likelihood of the null hypothesis is given by Equation 20.

$$L_{H_0}(R) = \Sigma_{i=1}^{n} x_i \log(1 - F_N) + (1-x_i)\log(F_N) \quad (20)$$

The Gaussian approximation can be used to obtain an estimate of the optimal censoring frequency f*. The Gaussian distribution of the sums for the two hypotheses are given by Equations 21 to 24.

$$\mu_1 = nB + nC(1 - E_{N-1}) \quad (21)$$

$$\sigma_1 = -C\sqrt{nE_{N-1}(1 - E_{N-1})} \quad (22)$$

$$\mu_0 = nB + nC(1 - F_N) \quad (23)$$

$$\sigma_0 = -C\sqrt{nF_N(1 - F_N)} \quad (24)$$

Using these Equations with Equation 14, the power is given by Equation 25.

$$1 - \beta = \Phi^{-1}\left\{\frac{z_\alpha \sqrt{F_N(1 - F_N)} - \sqrt{n}(E_{N-1} - F_N)}{\sqrt{E_{N-1}(1 - E_{N-1})}}\right\} \quad (25)$$

$\Phi$ is used (commonly in statistics literature) for the cumulative distribution function of the standard normal distribution. That is, if x is Normal with mean 0 and variance 1; $\Phi(t) = \text{Prob}(x < t)$ for any value of t. $\Phi^{-1}$ is the inverse of that function, i.e, if $\Phi^{-1}(s) = t$, that means $\Phi(t) = s$. It appears because if the values of $\mu_1$, $\sigma_1$, $\mu_0$, $\sigma_0$ are known (say from Equations 21 to 24), and one sets a desired limit on $\alpha$, one can solve Equation 14 to find $z(1-\beta)$ and estimate the statistical power of the test. The $\Phi^{-1}$ is needed to convert from $z(1-\beta)$ to the power $(1-\beta)$.

This example embodiment uses Equations 21 through 25, and the derivation of Equations 21 through 25 is not needed to practice the embodiment; therefore the derivation of Equations 21 through 25 is not repeated here. The derivation is incorporated by reference to the provisional application, as cited above. All terms in Equation 25 depend on f*, n, N, a, b, $\alpha$ and $\beta$. Thus, in a beacon with N individuals from a population with SFS parametrized by Beta(a-1, b-1) while allowing n queries given a desired false positive rate $\alpha$ and maximum allowable power $1-\beta$, one can find the censoring threshold f*. An analytical solution cannot be obtained for f* due to the form of the cumulative distribution function. However, a grid search over f* can be used to be find the optimal value for censoring threshold.

2.4 Simulation Embodiments

Simulations were performed with 500,000 SNPs in a sample of 1000 diploid individuals. Alternate allele frequencies were sampled from a multinomial distribution with probabilities obtained from the expected allele frequency distribution for standard neutral model assuming a population size of 10,000 individuals. A beacon was constructed using 1000 simulated individuals. The query set of individuals consisted of 200 diploid individuals from the beacon and 200 diploid individuals not in the beacon whose genotypes were simulated according to the generated allele frequencies at all SNPs. The false positive rate was set to 0.05 for all scenarios.

For initial experiments, the mismatch rate $\delta$ between the beacon and the 200 query copies of the same genomes was set to one part per million to simulate near ideal data quality.

The null distribution of the LRT statistic was obtained empirically using the exact test calculation for the 200 individuals not in the beacon. Power was calculated empirically as the proportion of the 200 tests for the query genomes in the beacon that were successfully rejected.

To examine if relatives could be identified from the beacon, 200 individuals from the beacon were used to generate query genomes with varying degrees of relatedness to the original individual.

Genome sequencing is more error-prone than array genotyping. Even with high coverage data, biological replicates of the same individual may have 1-5% SNPs unique to each replicate. On the same sequenced sample, different variant calling pipelines can produce SNP calls at positions that may differ from each other. This is modeled in the simulation by allowing for a mismatch probability $\delta$ that, for a query individual who is in the beacon and is heterozygous at the query SNP, the copy in the beacon is homozygous reference, i.e, the beacon will (erroneously) return 0 as the response to the query. Table 2 shows the levels of mismatch modeled in the simulated experiments.

TABLE 2

Error types modeled by mismatch rate $\delta$.

| Mismatch rate $\delta$ | Error type modeled |
|---|---|
| $10^{-6}$ | Ideal setting, almost zero noise |
| 0.001 | Genotype discordance between the same SNP in two replicates |
| 0.01 | Typical fraction of unique SNPs in two replicates |
| 0.1 | Upper bound on fraction of unique SNPs in two replicates |

Figure 8A:
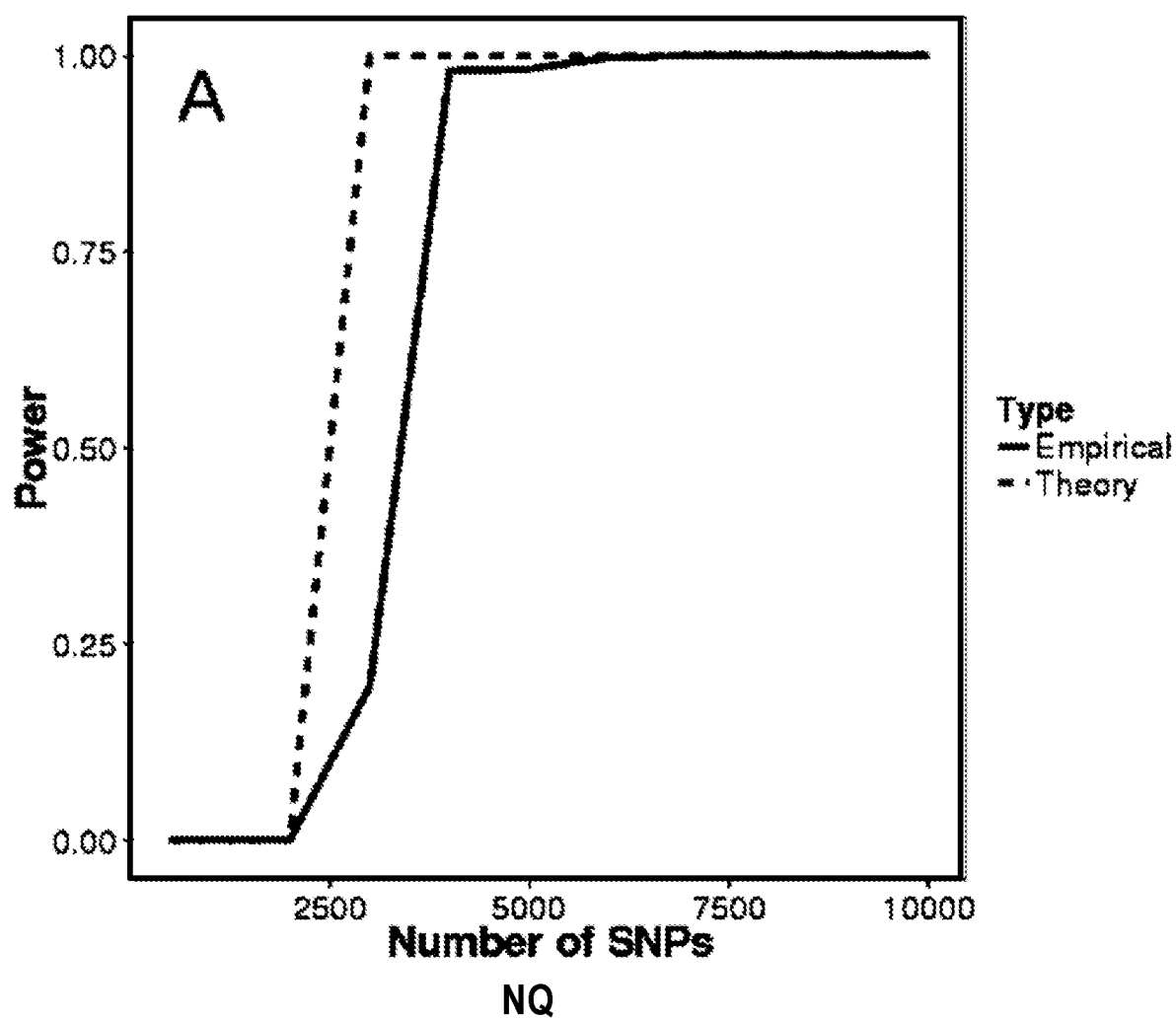
FIG. 8A is a graph that illustrates example power of the method for simulated data for an individual, according to an embodiment.

FIG. 8A is a graph that illustrates example power of the method for simulated data for an individual, according to an embodiment. The horizontal axis indicates the number of queries, NQ, each query asking whether a single SNP is present in the simulated beacon. The vertical axis indicates the power of test. The dashed line indicates the theoretical power given by Equation 13c, and the solid line gives the empirical power observed in the simulation. It can be seen that the LRT has more than 95% power for detecting whether an individual is in the beacon with just 5,000 SNP queries. It can also be seen that the theoretical analysis matches the empirical results very well.

Figure 8B:
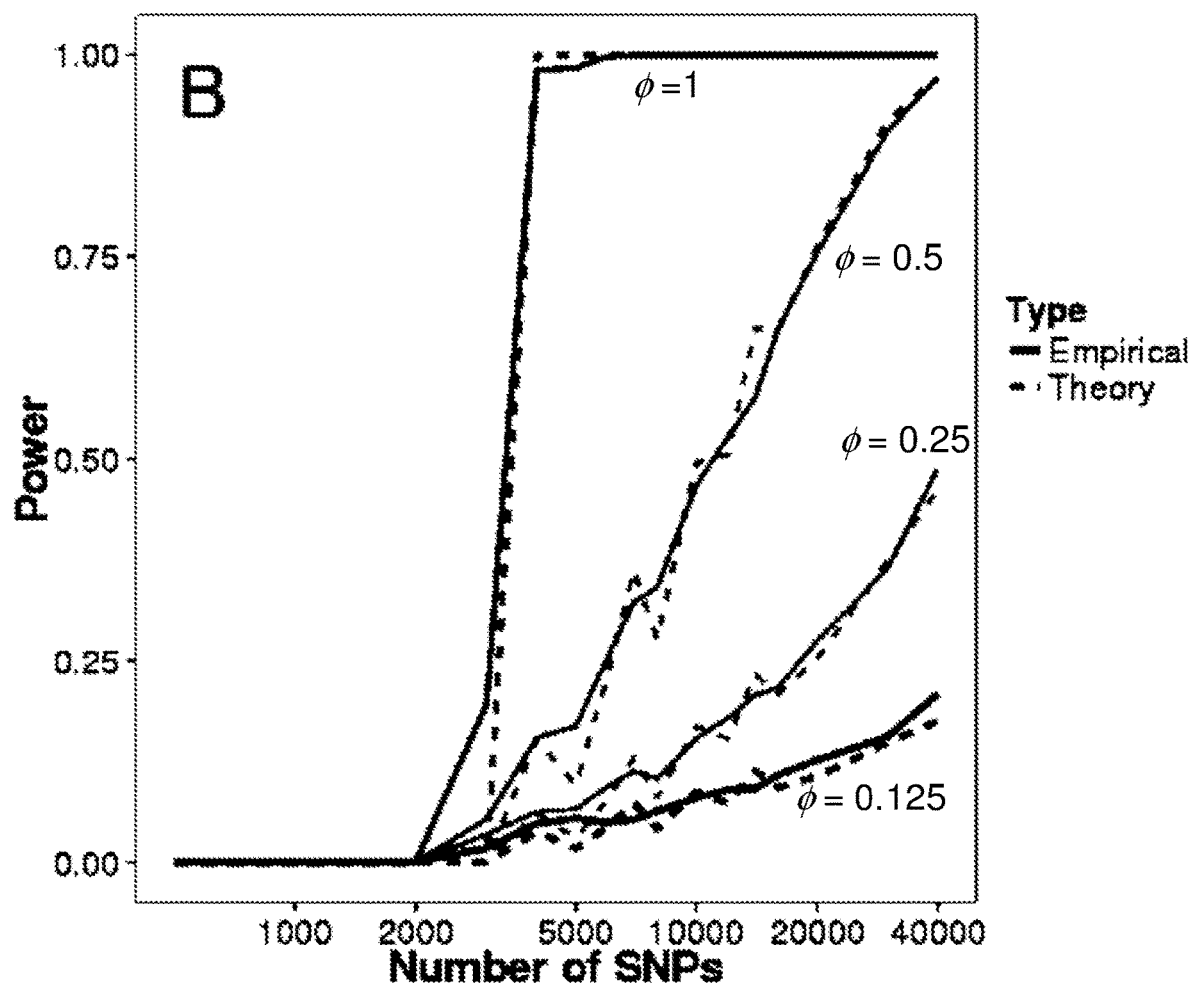
FIG. 8B is a graph that illustrates example power of the method for simulated data for relatives of an individual, according to an embodiment.
Figure 8C:
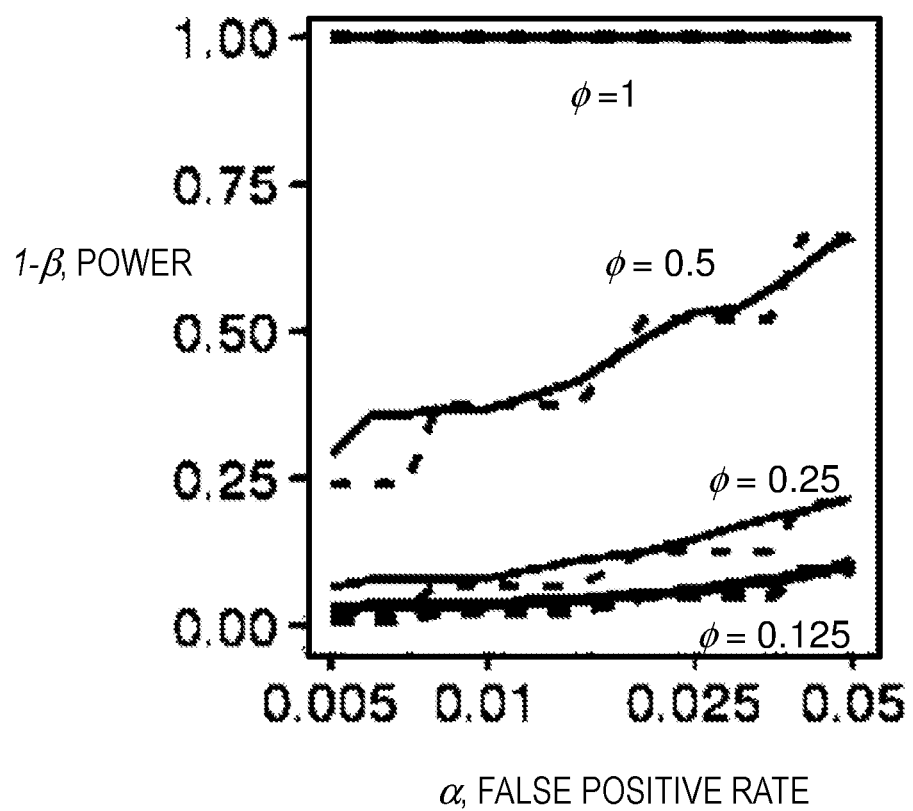
FIG. 8C is a graph that illustrates example power versus false positive rate in simulated data for relatives of an individual when the number of queries (NQ) is 16,000, according to an embodiment.

FIG. 8B is a graph that illustrates example power of the method for simulated data for relatives of an individual, according to an embodiment. The horizontal axis indicates the number of queries, NQ, each query asking whether a single SNP is present in the simulated beacon. The vertical axis indicates the power of test. The dashed line indicates the theoretical power given by Equation 13c, using Equation 16d for the binomial distribution of the alternative hypothesis, and the solid line gives the empirical power observed in the simulation. Pairs of theoretical and empirical powers are shown for each of four values of relatedness, for $\Phi=1$ (e.g., identical twin, which is the same cure as in FIG. 8A), 0.5, 0.25 and 0.125. For the same number of SNPs queried, the power for detecting relatives is reduced but still considerable. FIG. 8C is a graph that illustrates example power versus false positive rate in simulated data for relatives of an individual when NQ=16,000, according to an embodiment. Such curves are called ROC curves (for Receiver Operating Characteristic, named for historical uses) in statistics. The logarithmic horizontal axis indicates false positive rate (a) and the vertical axis indicates power $(1-\beta)$. With 16,000 queries, the power is useful for parents and non-identical siblings, $\phi=0.5$.

Figure 8D:
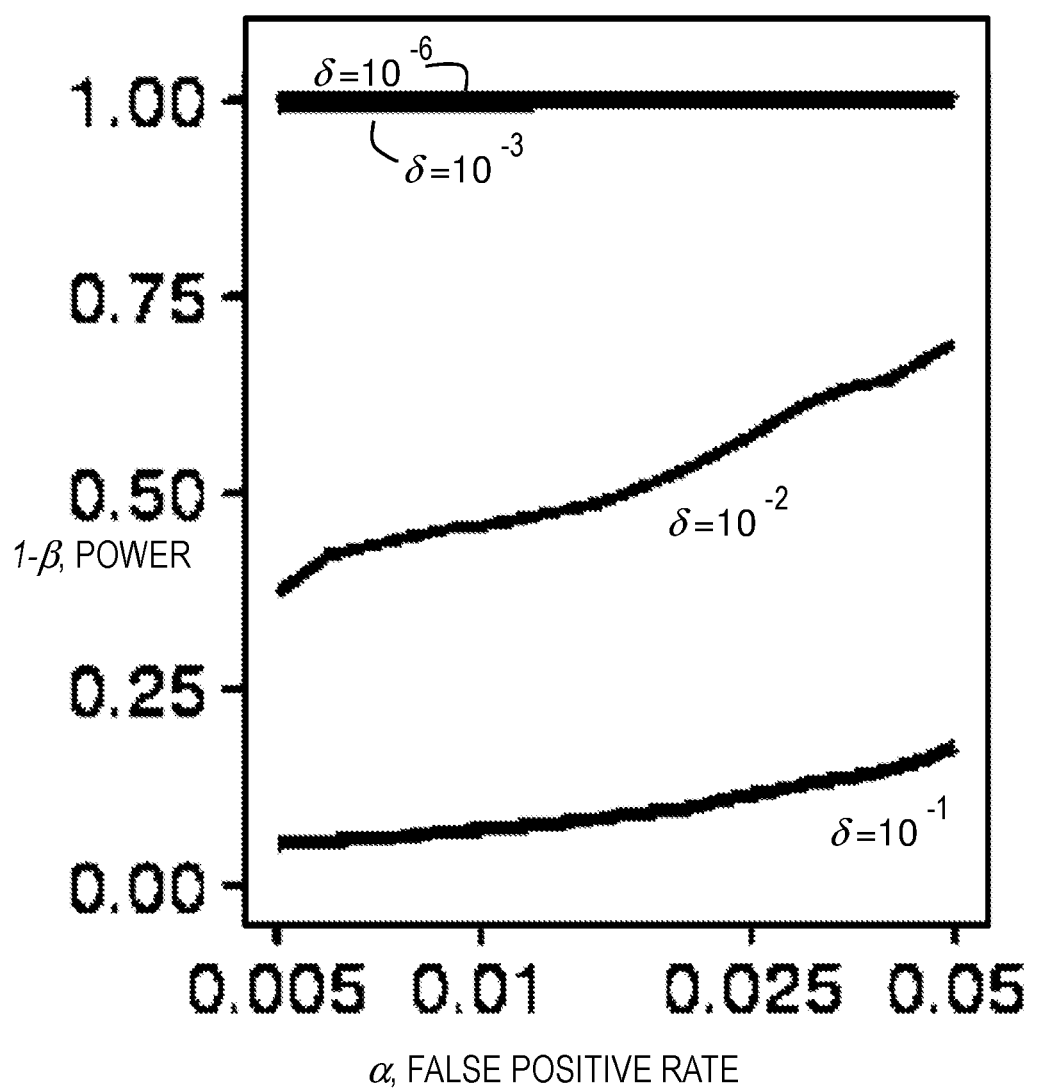
FIG. 8D is a graph that illustrates example power versus false positive rate in simulated data for different error rates when the number of queries (NQ) is 16,000, according to an embodiment.

FIG. 8D is a graph that illustrates example power versus false positive rate in simulated data for different error rates when NQ=16,000, according to an embodiment. The logarithmic horizontal axis indicates false positive rate ($\alpha$) and the vertical axis indicates power $(1-\beta)$. Empirical power and false alarm rates were determined when mismatch rates $\delta$ were set to $10^{-6}$, $10^{-3}$, $10^{-2}$ and $10^{-1}$. It can be seen that sequencing errors and variant calling differences reduce the power of the test, but error rates up to one in a hundred ($10^{-2}$) are well tolerated.

2.5 Real Data Embodiments

2.5.1 1000 Genomes Phase 1 CEU Beacon

A beacon was generated using the CEU (Western European) population from Phase 1 of the 1000 Genomes Project [8]. Of the 85 CEU samples present in Phase 1, 65 are used in the beacon. 20 samples from the beacon and the remaining 20 samples are used as query genomes. Whole genomes were then used to query the beacon, as before. To test if sharing SNP array data was more secure than sharing whole genomes, we repeated the setup with Affymetrix array data for the CEU samples. SNP array data was then used to query the beacon.

In some embodiments, the response from a beacon is based on the values of NQ and NY, as described above for step 423. In some of these embodiments, as described above, censoring is invoked to change the beacon response to queries for SNPs of low frequency in the beacon in order to protect the identity of individuals in the beacon. To test the effect of censoring on power, a beacon was constructed using the same data as above, except that the beacon always responded "No" to each query for a SNP that is a singleton in the beacon.

Figure 9A:
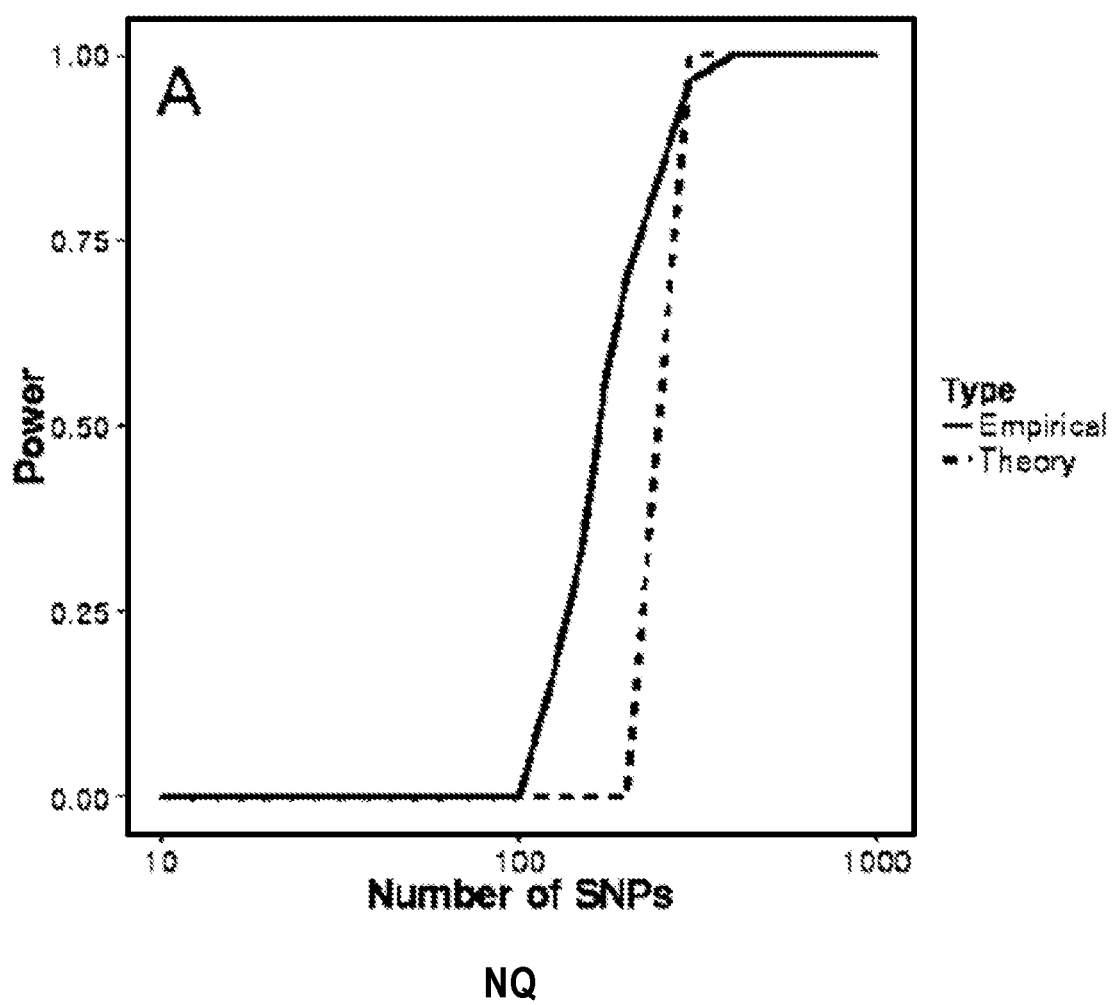
FIG. 9A is a graph that illustrates example power of the method for real data for an individual, according to an embodiment.
Figure 9B:
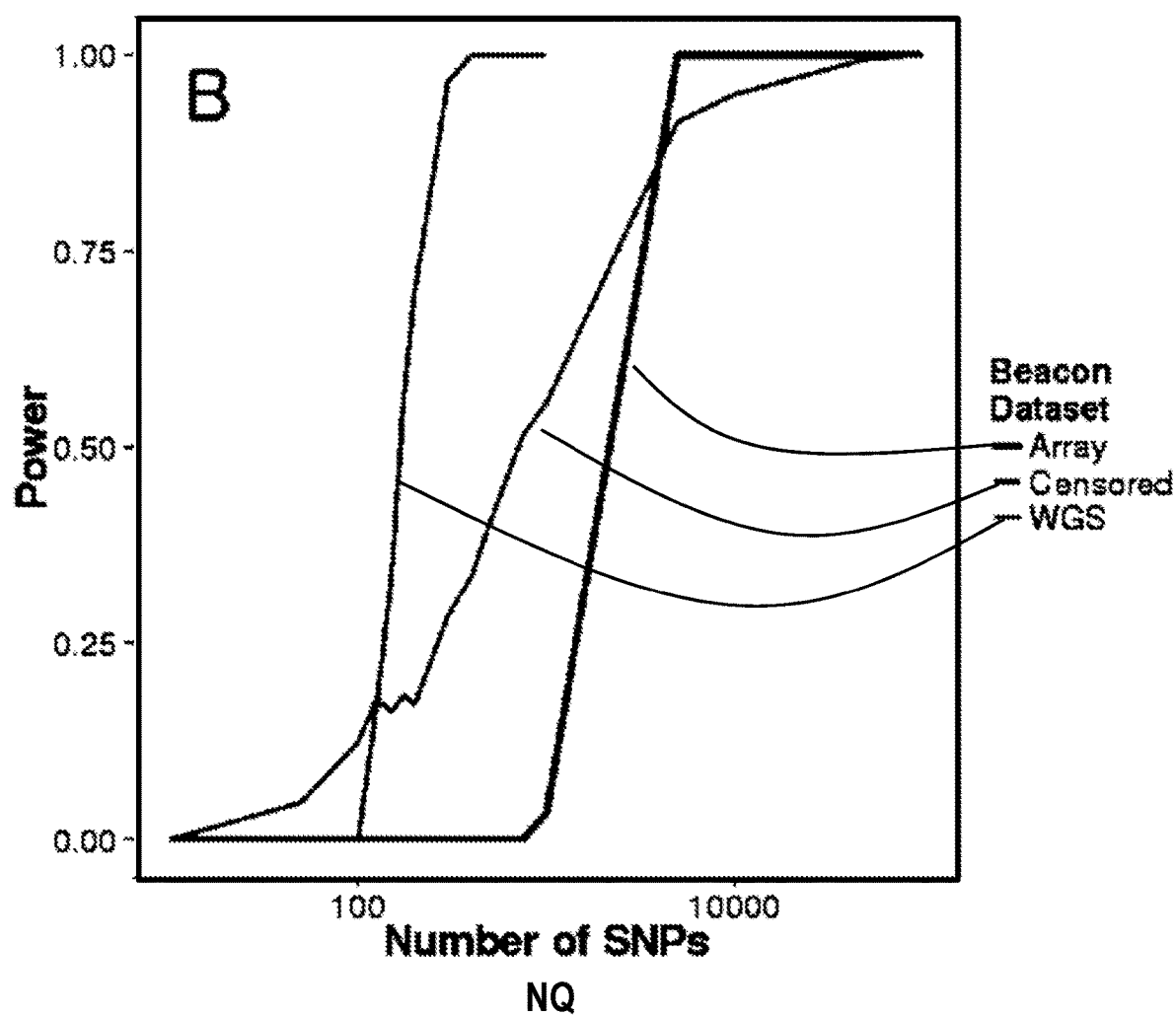
FIG. 9B is a graph that illustrates example power of the method for real data for an individual using censored or SNP beacon responses, according to an embodiment.

FIG. 9A is a graph that illustrates example power of the method for real data for an individual, according to an embodiment. The horizontal axis indicates the number of queries, NQ. The vertical axis indicates the power of test. The dashed line indicates the theoretical power given by Equation 13c for a 5% false positive rate, and the solid line gives the empirical power observed in the data. Using just 250 SNPs, beacon membership can be detected with 95% power and 5% false positive rate. FIG. 9B is a graph that illustrates example power of the method for real data for an individual using censored or SNP beacon responses, according to an embodiment. The horizontal axis indicates the number of queries, NQ. The vertical axis indicates the power of test. A trace is shone for responses based on the microarray subset of SNPs, on the whole genome sequencing (WGS) data set (as plotted in FIG. 9A) and on the censored WGS data set for which a query for a SNP that is a singleton in the data set receives a "No" response from the beacon. A beacon constructed using the same individuals but with SNP array data shows a reduction in power, as does a beacon which uses sequence data but censors responses by always replying 'No' to queries for singletons. Even in these scenarios, the LRT has greater than 90% power if 10,000 or more queries are permitted.

2.5.2 Beacons from Multiple Datasets

Figure 10A:
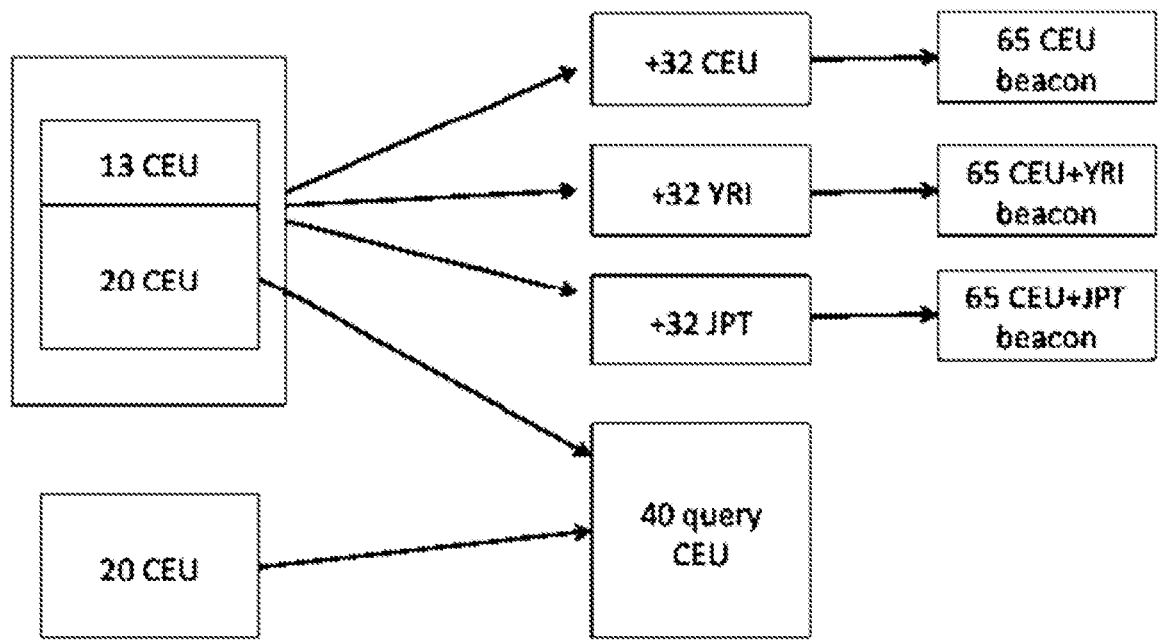
FIG. 10A is a block diagram that illustrates example beacons constructed from multiple datasets, according to an embodiment.

FIG. 10A is a block diagram that illustrates example beacons constructed from multiple datasets, according to an embodiment. CEU indicates an SNP reference panel based on central European, Ukraine genomes; JPT indicates an SNP reference panel based on Japan, Tokyo genomes; and, YRI indicates an SNP reference panel based on Yoruba of Ibadan, Nigeria genomes. As depicted in FIG. 10A, multiple beacons were constructed that contained either a single population (65 CEU individuals) or multiple populations (a CEU+YRI beacon with 32 CEU and 33 YRI individuals and a CEU+JPT beacon with 32 CEU and 33 JPT individuals). 40 CEU individuals were used as query individuals, with 20 belonging to all beacons and 20 belonging to none of the beacons.

From the theoretical analysis, one can see that increasing beacon size increases the number of SNPs required to achieve a given power level at a specified false positive rate threshold. Combining multiple datasets can make detection more difficult in the same way. A question of interest is whether combining multiple datasets can also make detection more difficult by affecting the SFS of the samples in the beacon.

Figure 10B:
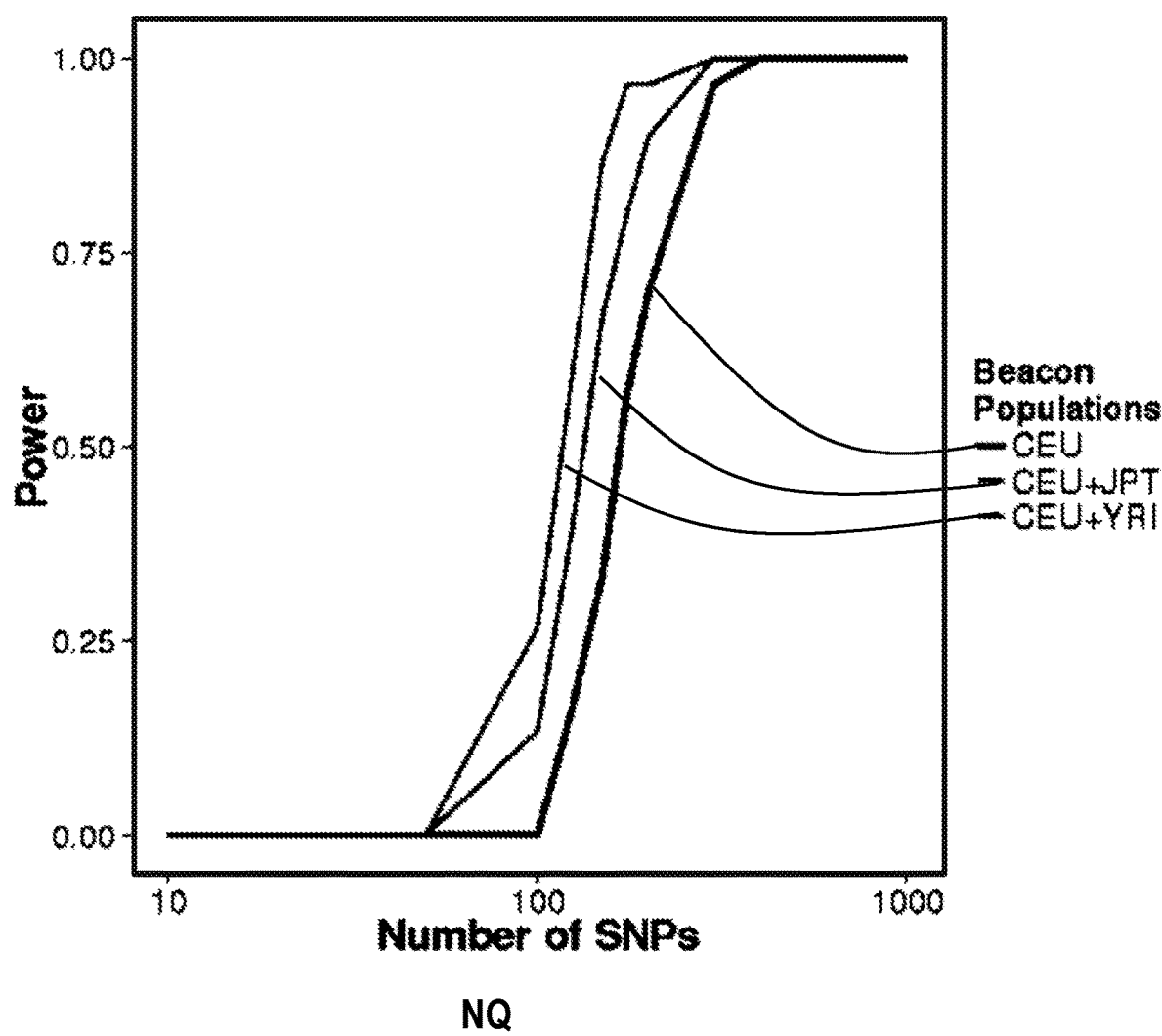
FIG. 10B is a graph that illustrates example power of tests for beacons containing multiple populations, according to various embodiments.

FIG. 10B is a graph that illustrates example power of tests for beacons containing multiple populations, according to various embodiments. The horizontal axis indicates the number of queries, NQ. The vertical axis indicates the power of test. A trace is plotted for each of the three beacon populations. The results show that for a fixed number of SNPs to query, the power for the multi-population beacons is higher than that for the CEU-only beacon. A single-population beacon is therefore more secure than a multi-population beacon of the same size. Since the protective effect of extra samples in the beacon against re-identification depends on their allele sharing with the query genome, including other populations in a beacon is less effective than including the same number of individuals from the population of the query genome.

2.5.3 Attacks on Existing Beacons

To test the method on existing beacons, a single genome (id: hu48C4EB or PGP 183) from the Personal Genome Project (Church 2005) was selected. 1000 heterozygous SNPs were chosen from the selected individual's genome. The Beacon Network query interface was used to query all existing beacons for the alternate allele at the chosen SNPs. If a beacon of size N produced k "Yes" responses to n queries, the p-value was calculated under the null hypothesis as $P(x \geq k; x\ Binomial(n, 1-D_N))$. To avoid overloading the beacon servers, a delay of 5 seconds was inserted between queries, and all 1000 queries were completed in 3 hours 53 minutes from a single computer. For the beacons of known size, the results are shown in Table 3. Based on the metadata alone, it was possible to ascertain that the selected individual was present in the PGP beacon and the Known VARiants (Glusman 2011) beacon, respectively. Both gave 100% yes responses. Yet only the PGP would reject the null hypothesis that the individual is not in the ensemble; and thus, with 1000 queries, conclude that the individual is in the beacon. The size of the Known VARiants beacon is so large that 1000 queries is not nearly enough to make a determination to reject the null hypothesis, demonstrating that re-identification is more difficult in larger beacons.

TABLE 3

Existing Beacons with known size.

| Beacon Name | Beacon Size | "Yes" Responses | P-value |
| --- | --- | --- | --- |
| Known VARiants | 72,000 | 1000 | 0.98 |
| Broad Institute | 60,706 | 27 | 1 |
| 1000 Genomes Project | 1,092 | 711 | 1 |
| PGP | 174 | 1000 | 0.0033 |
| Cafe CardioKit | 1,070 | 0 | 1 |
| Wellcome Trust Sanger Institute | 11,492 | 960 | 1 |
| NCBI | 14,466 | 947 | 1 |
| ICGC | 12,807 | 134 | 1 |
| AMPLab | 2,535 | 946 | 1 |
| 1000 Genomes Project - Phase 3 | 2,535 | 946 | 1 |

The theoretical analysis was used to estimate the number of queries required to re-identify individuals and relatives from existing beacons. Publicly available beacon metadata was used to infer the number of individuals present in the beacon. Where this was not possible (the AMPlab, ICGC and NCBI beacons), conservative estimates were used based on the size of the underlying datasets. For SFS parameters, the estimates for the simulation data, described above, were used. The Known Variants beacon contained 63,500 exomes and 8,400 whole genomes. Since exomes are only 1% of entire genomes in length, this beacon can be assumed to consist of two beacons: an exome beacon with 72,000 exomes; and a genome beacon with 8,400 whole genomes. Re-identification is possible in the genome beacon by avoiding queries for SNPs in the coding regions. The results of the computation for multiple existing beacons are summarized in Table 4.

TABLE 4

Estimated number of SNP queries (NQ) for re-identification in real beacons with a false positive rate of 5% and a power of 95%.

| Beacon | Number of samples | SNPs required for re-identification | | |
|---|---|---|---|---|
| | | Identical genomes | First-degree relatives | Second-degree relatives |
| 1000 Genomes Project | 1,092 | 3,649 | 34,467 | 157,861 |
| 1000 Genomes Project Phase 3 | 2,535 | 8,469 | 79,976 | 366,276 |
| AMPLab | 2,535 | 8,469 | 79,976 | 366,276 |
| Broad Institute | 60,706 | 202,770 | 1,914,581 | 8,768,007 |
| Cafe CardioKit | 1,070 | 3,575 | 33,773 | 154,684 |
| ICGC | 12,807 | 42,779 | 403,936 | 1,849,878 |
| Known VARiants | 72,000 | 240,494 | 2,270,772 | 10,399,218 |
| Known VARiants (genomes only) | 8,400 | 28,059 | 264,947 | 1,213,368 |
| NCBI | 14,466 | 48,320 | 456,258 | 2,089,490 |
| PGP | 174 | 582 | 5,515 | 25,273 |
| IBD | 5,070 | 16,936 | 159,926 | 732,410 |
| Native American + Egyptian | 100 | 335 | 3,181 | 14,586 |
| UK10K | 6,322 | 21,118 | 199,411 | 913,239 |
| SFARI | 10,400 | 34,739 | 328,024 | 1,502,231 |

From Table 4, it is seen that only the Broad Institute exome beacon and the Known VARiants exome beacon are safe from our re-identification attack, needing in excess of 200,000 queries to determine if an individual is included. This is because exomes have much fewer SNPs than genomes and so have fewer low frequency SNPs that can give away identification of individuals For all other beacons, re-identification is possible with 95% power, using less than 50,000 allele queries. Thus the approach is computationally feasible with most existing beacons.

In the illustrated embodiments, the proposed LRT provides a demonstration that individual privacy can be compromised through beacons. The illustrated embodiment was presented to show that beacon membership can be identified using only the query genome, even if allele frequencies are not known. As a result, the bounds obtained for the number of queries required for re-identification (Table 4) are conservative and need not be used directly to guide the construction of beacons. In other embodiments, a re-identification test that uses only rare SNPs and/or incorporates the allele frequencies at SNPs is expected to be more powerful than the illustrated embodiment and will require fewer queries than the estimates of Table 4.

The empirical power of the test does not depend on the SFS parameters. The power of the test is similar for populations with different SFS parameters and FIG. 9A shows good agreement between theoretical and empirical power curves on the CEU beacon. This suggests that the test is robust to different SFS parameters.

A computational performance limitation is that establishing high confidence may need millions of queries, which can take many months to perform. In the above experimental embodiments with existing beacons, 1000 queries to the beacon server (for all beacons) was made in 3 hours 53 minutes, with a 5 second delay between queries accounting for 1.4 hours of the total time.

In the illustrated embodiments, some simplifying assumptions were made. In other embodiments, other assumptions are made and still provide estimates of NQ and NY to achieve a certain degree of confidence in the results. For example, it is assumed above that the beacon samples and the query genome belong to the same population. This is a reasonable assumption since beacons often publish the ethnicity of the datasets included while the ethnicity of the query genome can be identified by comparing it to reference panels like 1000 Genomes. Genotypes are assumed to be distributed according to Hardy-Weinberg equilibrium. It is also assumed that allele queries are independent, which can lead to overly confident predictions for common SNPs. It is expected that this assumption will not affect these results significantly, since most SNPs are rare (<5% frequency) in human populations.

2.6 Enhanced Beacon Security

It is valuable to determine how beacons should be modified in some embodiments to protect against such attacks as summarized in Table 4.

The likelihood ratio test for identifying whether a given individual genome is part of a beacon has been developed, such as described above. These experiments show that in a variety of settings, re-identification is possible with high power for not only individuals in the beacon but also their relatives. Since beacons are often designed to share samples with a certain phenotype, this also discloses phenotype information about the individual who is detected to be part of the beacon. While detecting membership does not breach privacy, disclosure of potentially sensitive phenotype information is a serious privacy breach. Of the eight beacons listed in Table 4 which index genomic data that is not publicly available, four are associated with a single phenotype (Cafe CardioKit, ICGC, IBD, SFARI beacons), three are associated with multiple phenotypes (Broad Institute, NCBI, UK10K beacons) and one is not associated with any phenotype (Native American+Egyptian beacon). Table 5 lists the phenotypes associated with various beacons.

TABLE 5

Phenotypes linked with genomic data from existing beacons

| Beacon | Public data | Phenotype |
|---|---|---|
| 1000 Genomes Project | Yes | N.A. |
| 1000 Genomes Project Phase 3 | Yes | N.A |
| AMPLab | Yes | N.A. |
| Broad Institute | No | Mixture of phenotypes |
| Cafe CardioKit | No | Cardiac diseases |
| ICGC | No | Cancer |
| Known VARiants | Yes | N.A. |
| NCBI | No | Mixture of phenotype |
| PGP | Yes | N.A. |
| IBD | No | Inflammatory bowel disease |
| Native American + Egyptian | No | None |
| UK10K | No | Mixture of phenotypes |
| SFARI | No | Autism spectrum disorder |

A dataset is denoted as "public" if individual-level genotype data can be downloaded with requesting access. Beacons which index non-public data are shown in bold. For beacons indexing public data, the phenotype is listed as "N.A." (not applicable).

If the LRT described above (with false positive rate $\alpha=5\%$) identifies an individual as belonging to a case-only beacon (e.g., rejects the null hypothesis) for a disease with population prevalence (prior probability of an individual having the disease) $p=1\%$, then the posterior probability of the individual having the disease is given by $(1-\alpha)+\alpha p=0.9505$ according to Bayes' theorem. For the same result in a case-control beacon with equal numbers of cases and controls, the probability of the individual having the disease is given by $0.5*(1-\alpha)+0.05p=0.4755$. In contrast, while genomic risk prediction has high success rates for mendelian diseases with highly penetrant alleles and in some cancers, the success of such approaches for predicting common disease risk is modest (Shrodi 2014). An upper bound on the performance of genomic risk prediction using an individual's genome can be obtained by considering the (broad-sense) heritability of the disease being studied. Polderman et al. (2015) examined the heritability of 17,804 human traits. From their analysis, one can see that 26 out of 43 ICD 10-ICF sub-chapter level disease categories have heritability less than 50%, suggesting that the performance of genomic risk prediction for many disease categories will be limited.

The above results have important implications for setting up beacons to allow data sharing while still protecting individual privacy. Beacons are designed to help researchers find datasets relevant to their research interests (e.g., containing an allele that the researchers may have previously found associated in a genome-wide association study, GWAS). Individual level genotype data is usually access-controlled (Zerhouni 2008) and a researcher may spend considerable time and effort applying for access, only to find that the dataset is not relevant to the researcher's study. An advantage of a beacon is that any researcher can use it to query access-controlled data without applying for access. This will allow researchers to establish if an access-controlled dataset might be of interest; and, then apply for access only for relevant datasets. Two desirable features in beacons might therefore be that they contain a single dataset (so researchers who find a relevant dataset by querying a beacon can get data access through a single request) and that they return accurate information about presence of rare alleles. Solutions to protect privacy in beacons advantageously also maintain the utility of beacons by supporting these features.

Here are examined two ways in which security can be improved for anonymous-access beacons: (1) making detection of membership in the beacon more difficult, and (2) reducing the leakage of phenotype information from the beacon.

A number of approaches can be used make detection of membership in the beacon more difficult. Increasing beacon size can make detection more difficult as demonstrated above for the Known VARiant beacon. However, a disadvantage of this approach is some circumstances is that protection against genome-wide re-identification attacks will involve including tens of thousands of individuals. Another approach is to limit the genome region in the beacons. Beacons sharing small genomic regions (single genes or exomes) are more secure than those sharing whole genomes because there are fewer low frequency SNPs that give strong indication of individual membership. Confining a beacon to one population type provides more security for a given number of members. As demonstrated in FIG. 10B, beacons containing multiple populations are less secure than single-population beacons of the same size. Publishing metadata, such as the ethnicity of samples, beacon size or the names of datasets included, reduces beacon security. Conversely limiting the metadata about the beacons is advantageous to enhance security. Limiting the number and/or rate of queries per IP address can slow down attackers and are therefore not as effective as some of the other approaches. Data anonymization (Erlich 2014) approaches, such as using only common variation or censoring (FIG. 9B) make re-identification more difficult but not impossible. All of these methods make detection of membership in the beacon more difficult and can be combined in some embodiments, but these approaches can also reduce the utility of beacons to some users. Thus such approaches should be applied with caution and an eye to the expected utility of the beacon.

An alternative way of improving beacon security is to address the leakage of phenotype information, instead of or in addition to, reducing the possibility of re-identification. As described earlier, the probability that a re-identified sample has the disease associated with the beacon dataset depends on the proportion of cases in the beacon dataset. Therefore, by adding a suitable number of controls or aggregating responses from multiple beacons, the probability that a re-identified sample has the disease may be reduced to an acceptable level. Heritability estimates can be used to determine an acceptable probability level for a particular disease. These solutions reduce the phenotype information that can be obtained from a beacon with a minor reduction in the utility of the beacon due to the inclusion of non-case samples.

It is expected that, due to the lack of monitoring and access control, anonymous-access beacons will always be open to re-identification attempts. To improve security and reduce loss of privacy through beacons, it is advantageous to prohibit anonymous access. Requiring users to authenticate to access beacons will allow the research community to discourage re-identification attacks through policies outlining acceptable uses of beacons (Erlich 2014), which can be enforced against authorized users.

3. COMPUTATIONAL HARDWARE

Figure 5:
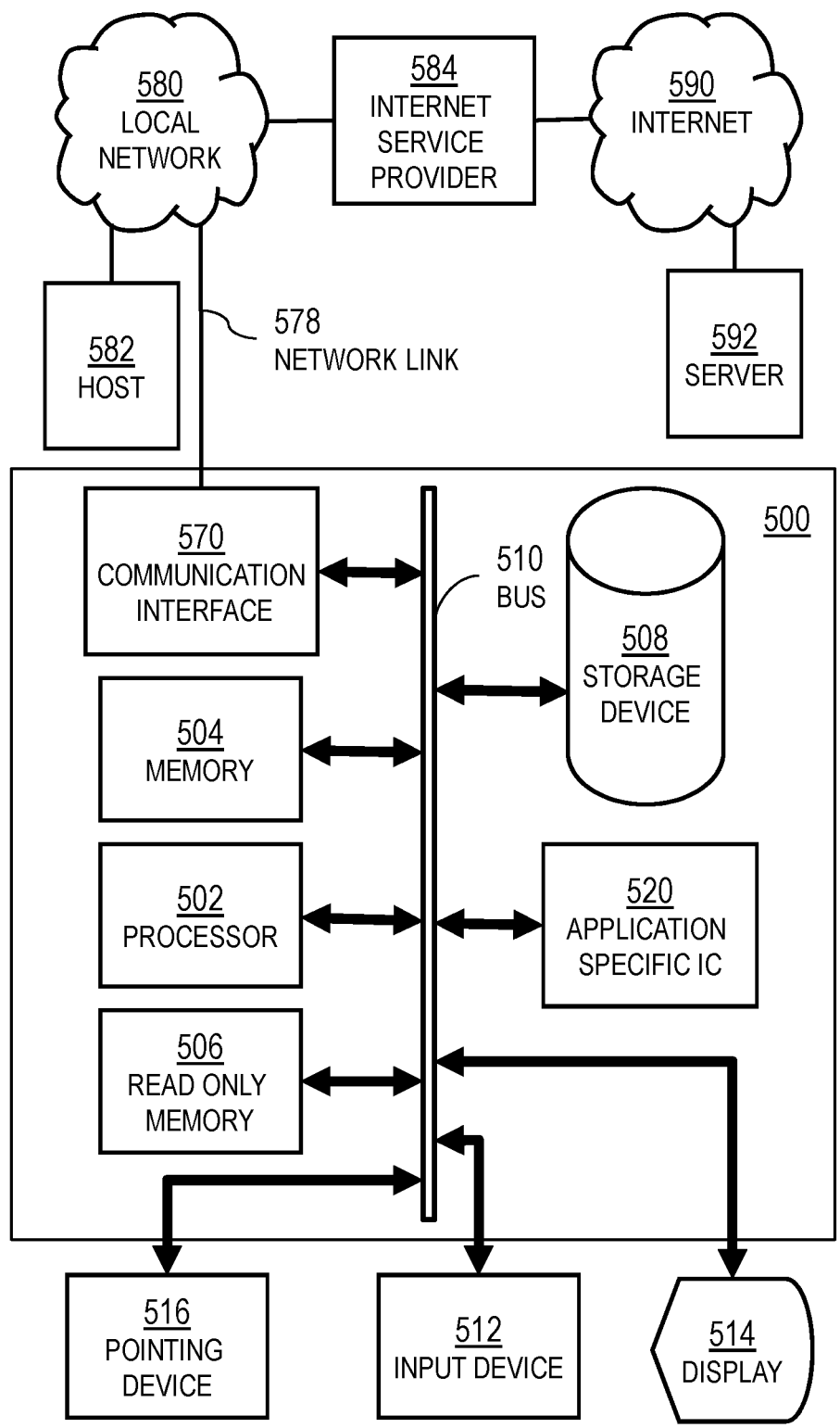
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 500, or a portion thereof, constitutes a means for performing one or more steps of one or more methods described herein.

A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitutes computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 570 sends and receives electrical, acoustic or electromagnetic signals, including infrared and optical signals that carry information streams, such as digital data.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 502, except for carrier waves and other signals.

Logic encoded in one or more tangible media includes one or both of processor instructions on a computer-readable storage media and special purpose hardware, such as ASIC 520.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, carry information to and from computer system 500. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a signal on a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to a signal on an infra-red a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

Figure 6:
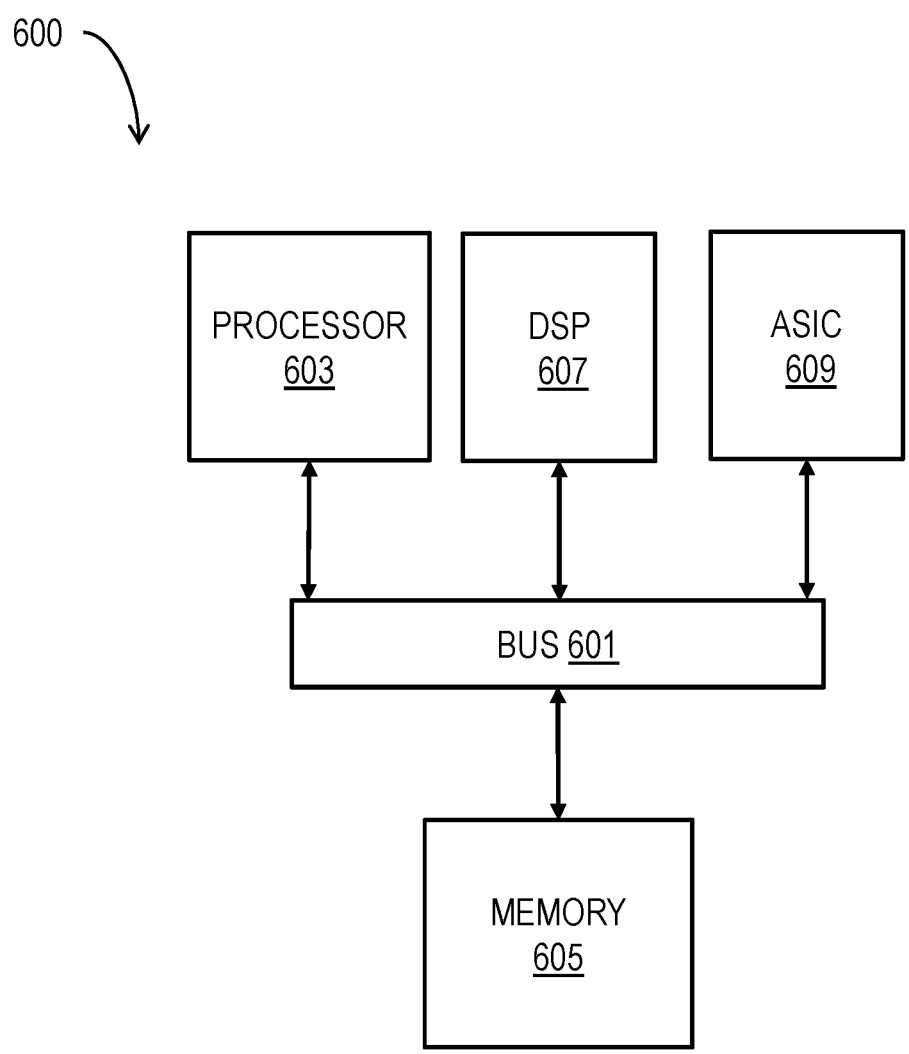
FIG. 6 illustrates a chip set upon which an embodiment of the invention may be implemented.

FIG. 6 illustrates a chip set 600 upon which an embodiment of the invention may be implemented. Chip set 600 is programmed to perform one or more steps of a method described herein and includes, for instance, the processor and memory components described with respect to FIG. 5 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 600, or a portion thereof, constitutes a means for performing one or more steps of a method described herein.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 605 also stores the data associated with or generated by the execution of one or more steps of the methods described herein.

4. ALTERNATIVES, EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

5. REFERENCES

1000 Genomes Project Consortium. 2012. An integrated map of genetic variation from 1,092 human genomes. Nature 491(7422):56-65.

Church, G. M. 2005. The personal genome project. Molecular systems biology 1(1):E1-E3.

Clayton, David. On inferring presence of an individual in a mixture: a Bayesian approach. 2010. Biostatistics 11(4): 661-73.

Erlich, Yaniv, and Arvind Narayanan. 2014. Routes for breaching and protecting genetic privacy. Nature Reviews: Genetics 15(6):409-21.

Erlich, Yaniv, James B. Williams, David Glazer, Kenneth Yocum, Nita Farahany, Maynard Olson, Arvind Narayanan, et al. 2014. Redefining genomic privacy: trust and empowerment. PLoS Biology 12(11):e1001983.

The Genome of the Netherlands Consortium. 2014. Whole-genome sequence variation, population structure and demographic history of the Dutch population. Nature Genetics 46(8):818-825.

Glusman, G., J. Caballero, D. E. Mauldin, L. Hood, and J. C. Roach. 2011. Kaviar: an accessible system for testing SNV novelty. Bioinformatics, 27(22):3216-3217.

Goldstein, Benjamin A, Lingyao Yang, Elias Salfati, and Themistoclies L. Assimes. 2015. Contemporary Considerations for Constructing a Genetic Risk Score: An Empirical Approach. Genetic Epidemiology 39(6):439-45.

Homer, Nils, Szabolcs Szelinger, Margot Redman, David Duggan, Waibhav Tembe, Jill Muehling, John V. Pearson, Dietrich A. Stephan, Stanley F. Nelson, and David W. Craig. 2008. Resolving individuals contributing trace amounts of DNA to highly complex mixtures using high-density SNP genotyping microarrays. PLoS Genetics 4(8):e1000167.

Jacobs, Kevin B., Meredith Yeager, Sholom Wacholder, David Craig, Peter Kraft, David J. Hunter, Justin Paschal, et al. 2009. A new statistic and its power to infer membership in a genome-wide association study using genotype frequencies. Nature Genetics 41(11):1253-7.

Polderman, Tinca J. C., Beben Benyamin, Christiaan A. de Leeuw, Patrick F. Sullivan, Arjen van Bochoven, Peter M. Visscher, and Danielle Posthuma. 2015. Meta-analysis of the heritability of human traits based on fifty years of twin studies. Nature Genetics, 47(7):702-709.

Rothstein, Mark A. 2008. Putting the Genetic Information Nondiscrimination Act in context. Genetics in Medicine 10(9):655-656.

Sankararaman, Sriram, Guillaume Obozinski, Michael I Jordan, and Eran Halperin. 2009. Genomic privacy and limits of individual detection in a pool. Nature Genetics 41(9):965-7.

Schrodi, Steven J., Shubhabrata Mukherjee, Ying Shan, Gerard Tromp, John J. Sninsky, Amy P. Callear, Tonia C. Carter, et al. 2014. Genetic-based prediction of disease traits: prediction is very difficult, especially about the future. Frontiers in Genetics 5:162.

Visscher, Peter M., and William G. Hill. 2009. The limits of individual identification from sample allele frequencies: theory and statistical analysis. PLoS Genetics, 5(10): e1000628.

Wei, Zhi, Wei Wang, Jonathan Bradfield, Jin Li, Christopher Cardinale, Edward Frackelton, Cecilia Kim, et al. 2013. Large sample size, wide variant spectrum, and advanced machine-learning technique boost risk prediction for inflammatory bowel disease. American Journal of Human Genetics, 92(6):1008-12.

Zerhouni, Elias A., and Elizabeth G. Nabel. 2008. Protecting aggregate genomic data. Science 322(5898):44.

Wong, Lai-Ping, RickTwee-Hee Ong, Wan-Ting Poh, Xuan-yao Liu, Peng Chen, Ruoying Li, KevinKoi-Yau Lam, et al. 2013. Deep Whole-Genome Sequencing of 100 Southeast Asian Malays. The American Journal of Human Genetics 92(1):52-66.

What is claimed is:

1. A method implemented on a hardware processor for determining membership of an individual in ensemble genomic data, which enables securing a system that manages genomic data to be shared on a network, the method comprising:

obtaining site frequency spectrum data, wherein the site frequency spectrum data indicates or approximates a number of different alleles, relative to a reference genome, in an ensemble of N unknown individuals, which alleles occurs a given multiple of times for several different multiples from 1 to N, or, when folded, the number of minor alleles in the ensemble without a reference genome, which occur a given multiple of times from 1 to N/2 in first ensemble genomic data aggregated for the ensemble;

determining the number N that indicates a number of individuals whose individual genomic data are aggregated in the first ensemble genomic data;

determining, based on the site frequency spectrum data and the number N, both a number NQ and a number NY, wherein the number NQ is a number of queries to employ, wherein each query requests whether a particular allele from an individual is present in the first ensemble genomic data, and the number NY is a number of yes responses that indicate a particular likelihood that the individual is a member of the ensemble; and providing output based on at least one of NQ or NY.

2. A method as recited in claim 1, wherein providing output based on at least one of NQ or NY further comprises providing from a system that manages the first ensemble genomic data responses to fewer than NQ different queries from a single source of queries within a predetermined time period.

3. A method as recited in claim 1, further comprising:

submitting, to a system that manages the first ensemble genomic data, NQ queries whether NQ different alleles present in an individual subject are present in the first ensemble genomic data; and determining whether the individual subject is a member of the ensemble based on responses to the NQ queries and the value of NY.

4. A method as recited in claim 3, wherein:

the method further comprises selecting at least NQ alleles at random from second genomic data determined for a sample collected from the individual subject; and submitting the NQ queries further comprises, for each of the at least NQ alleles selected at random from the second genomic data, submitting a query whether the allele is present in the first ensemble genomic data.

5. A method as recited in claim 3, wherein determining whether the individual subject is a member of the ensemble further comprises:

accumulating a number of affirmative responses to the at least NQ queries; and determining the particular likelihood that the individual subject is a member of the ensemble if the number of affirmative responses is equal to or greater than the threshold number NY.

6. A method as recited in claim 3, wherein providing output based on at least one of NQ or NY further comprises presenting on a display device output data that indicates the likelihood that the particular individual is a member of the ensemble.

7. A method as recited in claim 3, wherein obtaining the site frequency spectrum data further comprises determining the site frequency spectrum data based on a site frequency spectrum known for a population that is reasonably expected to be similar to the ensemble of unknown individuals.

8. A method as recited in claim 3, wherein determining the number N of individuals whose individual genomic data are aggregated in the first ensemble genomic data further comprises approximating the number N as a number reasonably expected to be greater than or equal to an unknown number of individuals in the ensemble.

9. A method as recited in claim 3, wherein the first ensemble genomic data is determined for a forensic sample collected at a scene of an incident to be investigated and the individual subject is one of a prospective victim or a prospective bystander or a prospective perpetrator.

10. A non-transitory computer-readable medium carrying one or more sequences of instructions for determining membership of an individual in ensemble genomic data, which enables securing a system that manages genomic data to be shared on a network, wherein execution of the one or more sequences of instructions by one or more processors causes an apparatus to:
obtain site frequency spectrum data, wherein the site frequency spectrum data indicates or approximates a number of different alleles, relative to a reference genome, in an ensemble of N unknown individuals, which alleles occurs a given multiple of times for several different multiples from 1 to N, or, when folded, the number of minor alleles in the ensemble without a reference genome, which occur a given multiple of times from 1 to N/2 in first ensemble genomic data aggregated for the ensemble;
determine the number N that indicates a number of individuals whose individual genomic data are aggregated in the first ensemble genomic data;
determine, based on the site frequency spectrum data and the number N, both a number NQ and a number NY, wherein the number NQ is a number of queries to employ, wherein each query requests whether a particular allele from an individual is present in the first ensemble genomic data, and the number NY is a number of yes responses that indicate a particular likelihood that the individual is a member of the ensemble; and
securing a system that manages the first ensemble genomic data to be shared on a network by providing output based on at least one of NQ or NY.

11. A non-transitory computer-readable medium as recited in claim 10, wherein providing output based on at least one of NQ or NY further comprises providing from a system that manages the first ensemble genomic data responses to fewer than NQ different queries from a single source of queries within a predetermined time period.

12. A non-transitory computer-readable medium as recited in claim 10, wherein execution of the one or more sequences of instructions by the one or more processors further causes the apparatus to:
submit, to a system that manages the first ensemble genomic data, NQ queries whether NQ different alleles present in an individual subject are present in the first ensemble genomic data; and
determine whether the individual subject is a member of the ensemble based on responses to the NQ queries and the value of NY.

13. A non-transitory computer-readable medium as recited in claim 12, wherein obtaining the site frequency spectrum data further comprises determining the site frequency spectrum data based on a site frequency spectrum known for a population that is reasonably expected to be similar to the ensemble of unknown individuals.

14. A non-transitory computer-readable medium as recited in claim 12, wherein determining the number N of individuals whose individual genomic data are aggregated in the first ensemble genomic data further comprises approximating the number N as a number reasonably expected to be greater than or equal to an unknown number of individuals in the ensemble.

15. A non-transitory computer-readable medium as recited in claim 12, wherein the first ensemble genomic data is determined for a forensic sample collected at a scene of an incident to be investigated and the individual subject is one of a prospective victim or a prospective bystander or a prospective perpetrator.

16. A system for determining membership of an individual in ensemble genomic data, which enables securing a system that manages genomic data to be shared on a network, the system comprising:
one or more hardware processors;
one or more computer-readable media; and
one or more sequences of instructions stored on the one or more computer readable media, wherein execution of the one or more sequences of instructions by the one or more processors causes an apparatus to:
obtain site frequency spectrum data, wherein the site frequency spectrum data indicates or approximates a number of different alleles, relative to a reference genome, in an ensemble of N unknown individuals, which alleles occurs a given multiple of times for several different multiples from 1 to N, or, when folded, the number of minor alleles in the ensemble without a reference genome, which occur a given multiple of times from 1 to N/2 in first ensemble genomic data aggregated for the ensemble;
determine the number N that indicates a number of individuals whose individual genomic data are aggregated in the first ensemble genomic data;
determine, based on the site frequency spectrum data and the number N, both a number NQ and a number NY, wherein the number NQ is a number of queries to employ, wherein each query requests whether a particular allele from an individual is present in the first ensemble genomic data, and the number NY is a number of yes responses that indicate a particular likelihood that the individual is a member of the ensemble; and
provide output based on at least one of NQ or NY.

17. A system as recited in claim 16, wherein providing output based on at least one of NQ or NY further comprises providing from a system that manages the first ensemble genomic data responses to fewer than NQ different queries from a single source of queries within a predetermined time period.

18. A system as recited in claim 16, wherein execution of the one or more sequences of instructions by the one or more processors further causes the apparatus to:
submit, to a system that manages the first ensemble genomic data, NQ queries whether NQ different alleles present in an individual subject are present in the first ensemble genomic data; and determine whether the individual subject is a member of the ensemble based on responses to the NQ queries and the value of NY.

19. A system as recited in claim 18, wherein determining the site frequency spectrum data further comprises determining the site frequency spectrum data based on a site frequency spectrum known for a population that is reasonably expected to be similar to the ensemble of unknown individuals.

20. A system as recited in claim 18, wherein determining the number N of individuals whose individual genomic data are aggregated in the first ensemble genomic data further comprises approximating the number N as a number reasonably expected to be greater than or equal to an unknown number of individuals in the ensemble.

21. A system as recited in claim 18, wherein the first ensemble genomic data is determined for a forensic sample collected at a scene of an incident to be investigated and the particular individual subject is one of a prospective victim or a prospective bystander or a prospective perpetrator.

* * * * *